United States Patent
Bara et al.

(10) Patent No.: US 12,428,381 B2
(45) Date of Patent: Sep. 30, 2025

(54) GAS TREATING SOLUTIONS CONTAINING IMIDAZOLE-AMINE COMPOUNDS AND METHODS OF MAKING THE SAME

(71) Applicant: The Board of Trustees of The University of Alabama, Tuscaloosa, AL (US)

(72) Inventors: Jason E. Bara, Tuscaloosa, AL (US); Kathryn E. O'Harra, Tuscaloosa, AL (US)

(73) Assignee: The Board of Trustees of The University of Alabama, Tuscaloosa, AL (US)

( * ) Notice: Subject to any disclaimer, the term of this patent is extended or adjusted under 35 U.S.C. 154(b) by 1201 days.

(21) Appl. No.: 17/220,206

(22) Filed: Apr. 1, 2021

(65) Prior Publication Data

US 2021/0371387 A1   Dec. 2, 2021

Related U.S. Application Data

(60) Provisional application No. 63/032,834, filed on Jun. 1, 2020.

(51) Int. Cl.
| | | |
|---|---|---|
| *B01D 53/02* | (2006.01) | |
| *B01D 53/14* | (2006.01) | |
| *C07D 233/64* | (2006.01) | |
| *C10L 3/10* | (2006.01) | |

(52) U.S. Cl.
CPC ....... *C07D 233/64* (2013.01); *B01D 53/1456* (2013.01); *B01D 53/1493* (2013.01); *C10L 3/104* (2013.01); *B01D 2252/20473* (2013.01); *C10L 2290/542* (2013.01)

(58) Field of Classification Search
None
See application file for complete search history.

(56) References Cited

U.S. PATENT DOCUMENTS

| | | |
|---|---|---|
| 8,506,914 B2 | 8/2013 | Bara |
| 8,741,246 B2 | 6/2014 | Bara |
| 10,350,544 B2 | 7/2019 | Bara |
| 2009/0291874 A1 | 11/2009 | Bara et al. |
| 2013/0143939 A1 | 6/2013 | Bara |
| 2017/0203250 A1* | 7/2017 | Koech ............... B01D 53/1493 |

FOREIGN PATENT DOCUMENTS

WO        2012135178        3/2012

OTHER PUBLICATIONS

Netl, Carbon Sequestration Technology Roadmap and Program Plan (2007), 48 pages.
Rochelle, G.T., "Amine Scrubbing for CO2 Capture," Science, 325:1652-1654 (2009).

* cited by examiner

*Primary Examiner* — Christopher P Jones
(74) *Attorney, Agent, or Firm* — Meunier Carlin & Curfman LLC

(57) ABSTRACT

Systems comprising a composition where an imidazole is tethered to an amine and a solvent are described herein. Methods of their preparation and use are also described herein. The methods of using the systems include the reduction of volatile compounds from gas streams and a liquid stream.

24 Claims, No Drawings

GAS TREATING SOLUTIONS CONTAINING IMIDAZOLE-AMINE COMPOUNDS AND METHODS OF MAKING THE SAME

CROSS-REFERENCE TO RELATED APPLICATIONS

This application claims the benefit of U.S. Provisional Application No. 63/032,834, filed Jun. 1, 2020, the content of which is incorporated herein in its entirety.

STATEMENT REGARDING FEDERALLY SPONSORED RESEARCH

This invention was made with government support under grant number DE-SC0018181, awarded by the Department of Energy. The government has certain rights in the invention.

FIELD

The subject matter disclosed herein generally relates to solutions comprising an imidazole tethered to an amine and a solvent. Also, the subject matter described herein generally relates to methods of using the systems described herein to capture and reduce volatile compounds from gas streams and liquid streams. Also, the subject matter described herein generally relates to methods of making imidazole-amine compounds.

BACKGROUND

There is a worldwide interest in capturing and sequestering or reusing carbon dioxide ($CO_2$) emissions to stabilize the climate. Aqueous amine processes, widely used throughout the natural gas industry to reduce $CO_2$ from gas streams via chemical reaction, represent the benchmark by which $CO_2$ capture technologies are evaluated (NETL, *Carbon Sequestration Technology Roadmap and Program Plan* (2007); Rochelle, G. T., "Amine Scrubbing for $CO_2$ Capture," *Science*, 325:1652-1654 (2009)). While effective at reducing $CO_2$ from gas streams, amine processes are highly energy-intensive, with much of the energy penalty attributed to boiling water during amine regeneration. Thus, aqueous amine processes will inherently suffer from large energy penalties. However, new solvents with little or no volatility can provide the desired energy efficiency.

Aqueous amine-based processes can suffer due to the relatively high vapor pressure of the amine compounds. Additionally, many of the amines utilized for carbon capture might not be cost-effective. Other strategies, such as the use of N-functionalized imidazoles (see Bara, J. E., WO 2012135178 A1, (2011)) or imido-acid salts (see Bara, J. E., U.S. Publication No. US 20130143939 A1 (2011)), have been previously suggested for $CO_2$ capture and storage.

Thus, there is a need for new systems designed to address the capturing of volatile compounds. There is also a need for methods of making such systems and methods of making the same. These needs and other needs are at least partially satisfied by the present disclosure.

SUMMARY

In accordance with the purposes of the disclosed materials, compounds, compositions, and methods, as embodied and broadly described herein, the disclosed subject matter, in one aspect, relates to compounds and compositions and methods for preparing and using such compounds and compositions.

In a further aspect, disclosed herein is a method for reducing one or more volatile compounds from a stream, comprising: contacting a stream with a solution comprising an imidazole having formula (I) and a solvent,

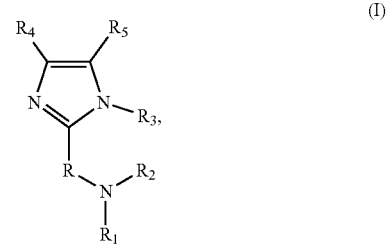

wherein
R is selected from null, $C_{1-20}$ alkyl, $C_{2-20}$ alkenyl, $C_{1-20}$ alkoxy, $C_{2-20}$ alkynyl, $C_{1-20}$ heteroalkyl, $C_{2-20}$ heteroalkenyl, $C_{2-20}$ heteroalkynyl, $C_6$-$C_{14}$ aryl, $C_1$-$C_{13}$ heteroaryl, $C_6$-$C_{14}$ aryloxy; wherein R is optionally substituted with $C_1$-$C_{20}$ alkyl, $C_1$-$C_{20}$ alkoxy, $C_2$-$C_{20}$ alkenyl, $C_2$-$C_{20}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl; and $R_1$ and $R_2$ are, independent of one another, hydrogen, $C_{1-20}$ alkyl, $C_{2-20}$ alkenyl, $C_1$-$C_{20}$ alkoxy, $C_{2-20}$ alkynyl, $C_{1-20}$ heteroalkyl, $C_{2-20}$ heteroalkenyl, $C_{2-20}$ heteroalkynyl, $C_6$-$C_{14}$ aryl, $C_1$-$C_{13}$ heteroaryl, $C_6$-$C_{14}$ aryloxy, carbonyl, ester, ether, halide, carboxyl, hydroxy, nitro, cyano, silyl, sulfo-oxo, sulfonyl, sulfone, sulfoxide, thiol, or phosphonyl; wherein each $R_1$ or $R_2$ independent of each other is optionally substituted with $C_1$-$C_{20}$ alkyl, $C_1$-$C_{20}$ alkoxy, $C_2$-$C_{20}$ alkenyl, $C_2$-$C_{20}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl;

$R_3$ is selected from hydrogen, $C_1$-$C_{10}$ alkyl, $C_1$-$C_{10}$ alkoxy, $C_6$-$C_{14}$ aryl, $C_1$-$C_{13}$ heteroaryl, $C_6$-$C_{14}$ aryloxy, wherein $R_3$ is optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl;

$R_4$ and $R_5$ are each independent of the other, selected from hydrogen, $C_{1-20}$ alkyl, $C_{2-20}$ alkenyl, $C_1$-$C_{20}$ alkoxy, $C_{2-20}$ alkynyl, $C_{1-20}$ heteroalkyl, $C_{2-20}$ heteroalkenyl, $C_{2-20}$ heteroalkynyl, $C_6$-$C_{14}$ aryl, $C_1$-$C_{13}$ heteroaryl, $C_6$-$C_{14}$ aryloxy, carbonyl, ester, ether, halide, carboxyl, hydroxy, nitro, cyano, silyl, sulfo-oxo, sulfonyl, sulfone, sulfoxide, thiol, or phosphonyl; wherein each $R_1$ or $R_2$ independent of each other is optionally substituted with $C_1$-$C_{20}$ alkyl, $C_1$-$C_{20}$ alkoxy, $C_2$-$C_{20}$ alkenyl, $C_2$-$C_{20}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl; or wherein $R_4$ and $R_5$ together form a 6 membered aromatic ring containing 6 carbon atoms.

Further provided herein are methods that include aspects where the imidazole of formula (I) absorbs the one or more volatile compounds. Yet further disclosed are aspects where the imidazole of formula (I) forms at least one complex with the one or more volatile compounds.

Also disclosed are aspects where the one or more volatile compounds present in the stream comprise one or more of carbon dioxide, hydrogen sulfide, sulfur dioxide, nitrogen oxide, nitrogen dioxide, carbonyl sulfide, or carbon disulfide.

Still further, methods for sweetening a natural gas feed stream are also provided herein. The methods comprise a) contacting the natural gas feed stream with a solution comprising an imidazole of formula (I) and a solvent,

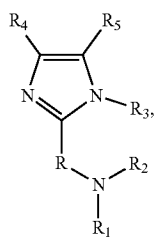

(I)

wherein
R is selected from null, $C_{1-20}$ alkyl, $C_{2-20}$ alkenyl, $C_{1-20}$ alkoxy, $C_{2-20}$ alkynyl, $C_{1-20}$ heteroalkyl, $C_{2-20}$ heteroalkenyl, $C_{2-20}$ heteroalkynyl, $C_6$-$C_{14}$ aryl, $C_1$-$C_{13}$ heteroaryl, $C_6$-$C_{14}$ aryloxy; wherein R is optionally substituted with $C_1$-$C_{20}$ alkyl, $C_1$-$C_{20}$ alkoxy, $C_2$-$C_{20}$ alkenyl, $C_2$-$C_{20}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl; and $R_1$ and $R_2$ are, independent of one another, hydrogen, $C_{1-20}$ alkyl, $C_{2-20}$ alkenyl, $C_1$-$C_{20}$ alkoxy, $C_{2-20}$ alkynyl, $C_{1-20}$ heteroalkyl, $C_{2-20}$ heteroalkenyl, $C_{2-20}$ heteroalkynyl, $C_6$-$C_{14}$ aryl, $C_1$-$C_{13}$ heteroaryl, $C_6$-$C_{14}$ aryloxy, carbonyl, ester, ether, halide, carboxyl, hydroxy, nitro, cyano, silyl, sulfo-oxo, sulfonyl, sulfone, sulfoxide, thiol, or phosphonyl; wherein each $R_1$ or $R_2$ independent of each other is optionally substituted with $C_1$-$C_{20}$ alkyl, $C_1$-$C_{20}$ alkoxy, $C_2$-$C_{20}$ alkenyl, $C_2$-$C_{20}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl;

$R_3$ is selected from hydrogen, $C_1$-$C_{10}$ alkyl, $C_1$-$C_{10}$ alkoxy, $C_6$-$C_{14}$ aryl, $C_1$-$C_{13}$ heteroaryl, $C_6$-$C_{14}$ aryloxy, wherein $R_3$ is optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl;

$R_4$ and $R_5$ are each independent of the other, selected from hydrogen, $C_{1-20}$ alkyl, $C_{2-20}$ alkenyl, $C_{1-20}$ alkoxy, $C_{2-20}$ alkynyl, $C_{1-20}$ heteroalkyl, $C_{2-20}$ heteroalkenyl, $C_{2-20}$ heteroalkynyl, $C_6$-$C_{14}$ aryl, $C_1$-$C_{13}$ heteroaryl, $C_6$-$C_{14}$ aryloxy, carbonyl, ester, ether, halide, carboxyl, hydroxy, nitro, cyano, silyl, sulfo-oxo, sulfonyl, sulfone, sulfoxide, thiol, or phosphonyl; wherein each $R_1$ or $R_2$ independent of each other is optionally substituted with $C_1$-$C_{20}$ alkyl, $C_1$-$C_{20}$ alkoxy, $C_2$-$C_{20}$ alkenyl, $C_2$-$C_{20}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl; or wherein $R_4$ and $R_5$ together form a 6 membered aromatic ring containing 6 carbon atoms;

b) forming a purified gas feed stream and a gas-rich solution; and c) separating the purified gas feed stream and the gas-rich solution.

In such methods, the imidazole of formula (I) is non-ionic under neutral conditions. The methods can further comprise regenerating the system by, for example, heating or pressurizing the gas-rich solution. The natural gas feed stream disclosed in the methods described herein can comprise one or more volatile compounds comprising one or more of carbon dioxide, hydrogen sulfide, sulfur dioxide, nitrogen oxide, nitrogen dioxide, carbonyl sulfide, or carbon disulfide.

Also disclosed herein is a solution for a reduction of volatile compounds, comprising a) an imidazole of formula (I),

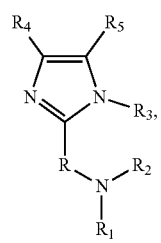

(I)

wherein
R is selected from null, $C_{1-20}$ alkyl, $C_{2-20}$ alkenyl, $C_{1-20}$ alkoxy, $C_{2-20}$ alkynyl, $C_{1-20}$ heteroalkyl, $C_{2-20}$ heteroalkenyl, $C_{2-20}$ heteroalkynyl, $C_6$-$C_{14}$ aryl, $C_1$-$C_{13}$ heteroaryl, $C_6$-$C_{14}$ aryloxy; wherein R is optionally substituted with $C_1$-$C_{20}$ alkyl, $C_1$-$C_{20}$ alkoxy, $C_2$-$C_{20}$ alkenyl, $C_2$-$C_{20}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl; and $R_1$ and $R_2$ are, independent of one another, hydrogen, $C_{1-20}$ alkyl, $C_{2-20}$ alkenyl, $C_1$-$C_{20}$ alkoxy, $C_{2-20}$ alkynyl, $C_{1-20}$ heteroalkyl, $C_{2-20}$ heteroalkenyl, $C_{2-20}$ heteroalkynyl, $C_6$-$C_{14}$ aryl, $C_1$-$C_{13}$ heteroaryl, $C_6$-$C_{14}$ aryloxy, carbonyl, ester, ether, halide, carboxyl, hydroxy, nitro, cyano, silyl, sulfo-oxo, sulfonyl, sulfone, sulfoxide, thiol, or phosphonyl; wherein each $R_1$ or $R_2$ independent of each other is optionally substituted with $C_1$-$C_{20}$ alkyl, $C_1$-$C_{20}$ alkoxy, $C_2$-$C_{20}$ alkenyl, $C_2$-$C_{20}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl;

$R_3$ is selected from hydrogen, $C_1$-$C_{10}$ alkyl, $C_1$-$C_{10}$ alkoxy, $C_6$-$C_{14}$ aryl, $C_1$-$C_{13}$ heteroaryl, $C_6$-$C_{14}$ aryloxy, wherein $R_3$ is optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl;

$R_4$ and $R_5$ are each independent of the other, selected from hydrogen, $C_{1-20}$ alkyl, $C_{2-20}$ alkenyl, $C_1$-$C_{20}$ alkoxy, $C_{2-20}$ alkynyl, $C_{1-20}$ heteroalkyl, $C_{2-20}$ heteroalkenyl, $C_{2-20}$ heteroalkynyl, $C_6$-$C_{14}$ aryl, $C_1$-$C_{13}$ heteroaryl, $C_6$-$C_{14}$ aryloxy, carbonyl, ester, ether, halide, carboxyl, hydroxy, nitro, cyano, silyl, sulfo-oxo, sulfonyl, sulfone, sulfoxide, thiol, or phosphonyl; wherein each $R_1$ or $R_2$ independent of each other is optionally substituted with $C_1$-$C_{20}$ alkyl, $C_1$-$C_{20}$ alkoxy, $C_2$-$C_{20}$ alkenyl, $C_2$-$C_{20}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl; or wherein $R_4$ and $R_5$ together form a 6 membered aromatic ring containing 6 carbon atoms; and b) a solvent.

In such exemplary aspects, the solvent can comprise one or more of water, tetrahydrofuran, dichloromethane, acetonitrile, toluene, dimethyl sulfoxide, pyridine, dimethylformamide, dioxane, glycol solvents, methanol, ethanol, propanol, butanol, ethyl acetate, methyl ethyl ketone, or acetone. In still further aspects, the solution is configured to absorb one or more volatile compounds comprising carbon dioxide, hydrogen sulfide, sulfur dioxide, nitrogen oxide, nitrogen dioxide, carbonyl sulfide, carbon disulfide, or mixtures thereof.

Also disclosed herein are methods of making an imidazole compound of formula (II) comprising: a) oxidizing a compound having a general formula of (III)

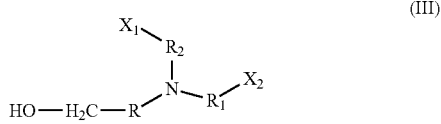

(III)

to form an aldehyde of general formula (IV):

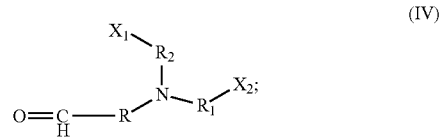

(IV)

b) reacting the aldehyde of formula (IV) with a dialdehyde compound of formula (V)

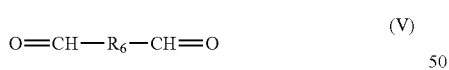

(V)

$$O=CH-R_6-CH=O$$

and an ammonium salt to form a compound of general formula (VI):

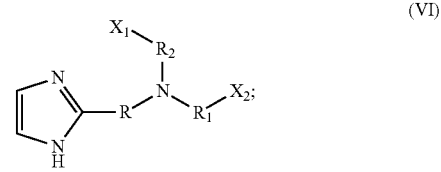

(VI)

and c) deprotecting the compound of formula (VI) to form the compound of formula (II):

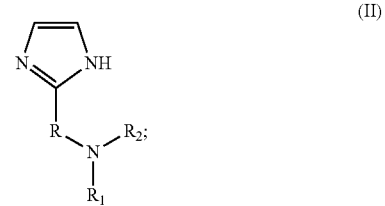

(II)

wherein

R is selected from null, $C_{1-20}$ alkyl, $C_{2-20}$ alkenyl, $C_1$-$C_{20}$ alkoxy, $C_{2-20}$ alkynyl, $C_{1-20}$ heteroalkyl, $C_{2-20}$ heteroalkenyl, $C_{2-20}$ heteroalkynyl, $C_6$-$C_{14}$ aryl, $C_1$-$C_{13}$ heteroaryl, $C_6$-$C_{14}$ aryloxy; wherein R is optionally substituted with $C_1$-$C_{20}$ alkyl, $C_1$-$C_{20}$ alkoxy, $C_2$-$C_{20}$ alkenyl, $C_2$-$C_{20}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl; and $R_1$ and $R_2$ are, independent of one another, hydrogen, $C_{1-20}$ alkyl, $C_{2-20}$ alkenyl, $C_1$-$C_{20}$ alkoxy, $C_{2-20}$ alkynyl, $C_{1-20}$ heteroalkyl, $C_{2-20}$ heteroalkenyl, $C_{2-20}$ heteroalkynyl, $C_6$-$C_{14}$ aryl, $C_1$-$C_{13}$ heteroaryl, $C_6$-$C_{14}$ aryloxy, carbonyl, ester, ether, halide, carboxyl, hydroxy, nitro, cyano, silyl, sulfo-oxo, sulfonyl, sulfone, sulfoxide, thiol, or phosphonyl; wherein each $R_1$ or $R_2$ independent of each other is optionally substituted with $C_1$-$C_{20}$ alkyl, $C_1$-$C_{20}$ alkoxy, $C_2$-$C_{20}$ alkenyl, $C_2$-$C_{20}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl;

$R_6$ is selected from null, $C_{1-20}$ alkyl, $C_{2-20}$ alkenyl, $C_1$-$C_{20}$ alkoxy, $C_{2-20}$ alkynyl, $C_{1-20}$ heteroalkyl, $C_{2-20}$ heteroalkenyl, $C_{2-20}$ heteroalkynyl, $C_6$-$C_{14}$ aryl, $C_1$-$C_{13}$ heteroaryl, $C_6$-$C_{14}$ aryloxy; wherein $R_6$ is optionally substituted with $C_1$-$C_{20}$ alkyl, $C_1$-$C_{20}$ alkoxy, $C_2$-$C_{20}$ alkenyl, $C_2$-$C_{20}$ alkenyl, $C_6$-$C_{14}$ aryl, $C_1$-$C_{13}$ heteroaryl, amino, carbonyl, ester, ether, halide, carboxyl, hydroxy, nitro, cyano, sulfo-oxo, sulfonyl, sulfone, sulfoxide, thiol, or phosphonyl; and $X_1$ and $X_2$ are protecting groups, each independently, selected from $C_6$-$C_{14}$ aryl, $C_1$-$C_{13}$ heteroaryl, $C_6$-$C_{14}$ aryloxy, benzyl, carbonyl, alkoxy, ether, cyclic ether; wherein each of $X_1$ and $X_2$ independent of each other is optionally substituted with $C_1$-$C_{20}$ alkyl, $C_1$-$C_{20}$ alkoxy, $C_2$-$C_{20}$ alkenyl, $C_2$-$C_{20}$ alkynyl, $C_6$-$C_{14}$ aryl, $C_1$-$C_{13}$ heteroaryl, amino, benzyl, carbonyl, ester, ether, halide, carboxyl, hydroxy, nitro, cyano, silyl, sulfo-oxo, sulfonyl, sulfone, sulfoxide, thiol, or phosphonyl.

The methods further comprise functionalizing the compound of formula (II) to obtain a compound of formula (I) as described above.

Additional advantages will be set forth in part in the description that follows and in part will be obvious from the description or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DETAILED DESCRIPTION

The materials, compounds, compositions, articles, and methods described herein may be understood more readily by reference to the following detailed description of specific aspects of the disclosed subject matter, and the Examples included therein.

Before the present materials, compounds, compositions, kits, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

It is appreciated that certain features of the disclosure, which are, for clarity, described in the context of separate aspects, can also be provided in combination in a single aspect. Conversely, various features of the disclosure, which are, for brevity, described in the context of a single aspect, can also be provided separately or in any suitable subcombinaton.

The term "comprising" and variations thereof as used herein is used synonymously with the term "including" and variations thereof and are open, non-limiting terms. Although the terms "comprising" and "including" have been used herein to describe various examples, the terms "consisting essentially of" and "consisting of" can be used in place of "comprising" and "including" to provide for more specific examples of the invention and are also disclosed. Other than in the examples, or where otherwise noted, all numbers expressing quantities of ingredients, reaction conditions, and so forth used in the specification and claims are to be understood at the very least and not as an attempt to limit the application of the doctrine of equivalents to the scope of the claims, to be construed in light of the number of significant digits and ordinary rounding approaches.

As used in the description and the appended claims, the singular forms "a," "an," and "the" include plural referents unless the context clearly dictates otherwise. Thus, for example, reference to "a composition" includes mixtures of two or more such compositions, reference to "the compound" includes mixtures of two or more such compounds and the like.

"Optional" or "optionally" means that the subsequently described event or circumstance can or cannot occur and that the description includes instances where the event or circumstance occurs and instances where it does not.

For the terms "for example" and "such as," and grammatical equivalences thereof, the phrase "and without limitation" is understood to follow unless explicitly stated otherwise.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Furthermore, when numerical ranges of varying scope are set forth herein, it is contemplated that any combination of these values inclusive of the recited values may be used. Further, ranges can be expressed herein as from "about" one particular value and/or to "about" another particular value. When such a range is expressed, another aspect includes from the one particular value and/or to the other particular value.

Similarly, when values are expressed as approximations, by use of the antecedent "about," it will be understood that the particular value forms another aspect. It will be further understood that the endpoints of each of the ranges are significant both in relation to the other endpoint and independently of the other endpoint. Unless stated otherwise, the term "about" means within 5% (e.g., within 2% or 1%) of the particular value modified by the term "about."

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6 and any whole and partial increments therebetween. This applies regardless of the breadth of the range.

By "reduce" or other forms of the word, such as "reducing" or "reduction," is meant lowering of an event or characteristic (e.g., volatile compounds in a stream). It is understood that this is typically in relation to some standard or expected value; in other words, it is relative, but that it is not always necessary for the standard or relative value to be referred to. For example, "reduces $CO_2$" means reducing the amount of $CO_2$ in a stream relative to a standard or a control. As used herein, the term "reduce" can include complete removal. In the disclosed method, reduction can refer to a 10%, 20%, 30%, 40%, 50%, 60%, 70%, 80%, 90%, or 100% decrease as compared to the standard or a control. It is understood that the terms "sequester," "capture," "remove," and "separation" are used synonymously with the term "reduce."

By "treat" or other forms of the word, such as "treated" or "treatment," is meant to add or mix two or more compounds, compositions, or materials under appropriate conditions to produce a desired product or effect (e.g., to reduce or eliminate a particular characteristic or event such as $CO_2$ reduction). The terms "contact" and "react" are used synonymously with the term "treat."

It is understood that throughout this specification, the identifiers "first" and "second" are used solely to aid in distinguishing the various components and steps of the disclosed subject matter. The identifiers "first" and "second" are not intended to imply any particular order, amount, preference, or importance to the components or steps modified by these terms.

The term "complex" is used herein does not mean to describe a particular type of bonding or coordination between the compounds disclosed herein but to indicate that the compounds described herein can be associated with each other in any possible configuration.

As used herein, the term or phrase "effective," "effective amount," or "conditions effective to" refers to such amount or condition that is capable of performing the function or property for which an effective amount or condition is expressed. As will be pointed out below, the exact amount or particular condition required will vary from one aspect to another, depending on recognized variables such as the materials employed and the processing conditions observed. Thus, it is not always possible to specify an exact "effective amount" or "condition effective to." However, it should be understood that an appropriate, effective amount will be readily determined by one of ordinary skill in the art using only routine experimentation.

Chemical Definitions

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight, component Y, X and Y are present at a weight ratio of 2:5 and are present in such ratio regardless of whether additional components are contained in the compound.

A weight percent (wt. %) of a component, unless specifically stated to the contrary, is based on the total weight of the formulation or composition in which the component is included.

The term "non-ionic" as used herein refers to being free of ionic groups or groups that are readily substantially ionized in water. A "non-ionic" compound does not contain a charge at neutral pH (e.g., at a pH from 6.7 to 7.3). However, non-ionic compounds can be made to have a charge under acidic or basic conditions or by methods known in the art, e.g., protonation, deprotonation, oxidation, reduction, alkylation, acetylation, esterification, de-esterification, hydrolysis, etc. Thus, the disclosed "non-ionic" compounds can become ionic under conditions where, for example, an acidic proton is available to protonate the compound.

The term "volatile compound," as used herein, refers to chemical compounds that are capable of vaporizing to a significant amount or that exist as a gas at ambient conditions. The "volatile compounds" described herein are found in the streams and have higher vapor pressures than the stream, such as natural gas feeds. Examples of volatile compounds include light gases and acid gases, such as $CO_2$, $O_2$, $N_2$, $CH_4$, $H_2$, hydrocarbons, $H_2S$, $SO_2$, $NO$, $NO_2$, $COS$, $CS_2$, and the like.

As used herein, the term "substituted" means that a hydrogen atom is removed and replaced by a substituent. It is contemplated to include all permissible substituents of organic compounds. As used herein, the phrase "optionally substituted" means unsubstituted or substituted. It is to be understood that substitution at a given atom is limited by valency. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein, which satisfy the valencies of the heteroatoms. This disclosure is not intended to be limited in any manner by the permissible substituents of organic compounds. Also, the terms "substitution" or "substituted with" include the implicit proviso that such substitution is in accordance with the permitted valence of the substituted atom and the substituent and that the substitution results in a stable compound, e.g., a compound that does not spontaneously undergo transformation such as by rearrangement, cyclization, elimination, etc. In still further aspects, it is understood that when the disclosure describes a group being substituted, it means that the group is substituted with one or more (i.e., 1, 2, 3, 4, or 5) groups as allowed by valence selected from alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

All compounds, and salts thereof, can be found together with other substances such as water and solvents (e.g., hydrates and solvates).

Compounds provided herein also can include tautomeric forms. Tautomeric forms result from the swapping of a single bond with an adjacent double bond together with the concomitant migration of a proton. Tautomeric forms include prototropic tautomers that are isomeric protonation states having the same empirical formula and total charge. Example prototropic tautomers include ketone—enol pairs, amide—imidic add pairs, lactam—lactim pairs, enamine—imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds provided herein can also include all isotopes of atoms occurring in the intermediates or final compounds. Isotopes include those atoms having the same atomic number but different mass numbers. For example, isotopes of hydrogen include hydrogen, tritium, and deuterium.

Also provided herein are salts of the compounds described herein. It is understood that the disclosed salts can refer to derivatives of the disclosed compounds wherein the parent compound is modified by converting an existing acid or base moiety to its salt form. Examples of the salts include, but are not limited to, mineral or organic acid salts of basic residues such as amines; alkali or organic salts of acidic residues such as carboxylic acids; and the like. The salts of the compounds provided herein include the conventional non-toxic salts of the parent compound formed, for example, from non-toxic inorganic or organic acids. The salts of the compounds provided herein can be synthesized from the parent compound that contains a basic or acidic moiety by conventional chemical methods. Generally, such salts can be prepared by reacting the free acid or base forms of these compounds with a stoichiometric amount of the appropriate base or acid in water or an organic solvent or in a mixture of the two. In various aspects, nonaqueous media like ether, ethyl acetate, alcohols (e.g., methanol, ethanol, isopropanol, or butanol) or acetonitrile (ACN) can be used.

In various aspects, the compounds provided herein, or salts thereof, are substantially isolated. By "substantially isolated," it meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

As used herein, chemical structures that contain one or more stereocenters depicted with dashed and bold bonds are meant to indicate absolute stereochemistry of the stereocenter(s) present in the chemical structure. As used herein, bonds symbolized by a simple line do not indicate a stereopreference. Unless otherwise indicated to the contrary, chemical structures, which include one or more stereocenters, illustrated herein without indicating absolute or relative stereochemistry encompass all possible stereoisomeric forms of the compound (e.g., diastereomers and enantiomers) and mixtures thereof. Structures with a single bold or dashed line and at least one additional simple line encompass a single enantiomeric series of all possible diastereomers.

The resolution of racemic mixtures of compounds can be carried out using appropriate methods. An exemplary method includes fractional recrystallization using a chiral resolving acid that is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid, or the various optically active camphorsulfonic adds such as camphorsulfonic acid. Other resolving agents suitable for fractional crystallization methods include stereoisomerically pure forms of methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent compositions can be determined by one skilled in the art.

The expressions "ambient temperature" and "room temperature" as used herein are understood in the art and refer generally to a temperature, e.g., a reaction temperature, that is about the temperature of the room in which the reaction is carried out, for example, a temperature from about 20° C. to about 30° C.

"$R^1$," "$R^2$," "$R^3$," "$R^4$," etc., are used herein as generic symbols to represent various specific substituents. These symbols can be any substituents, not limited to those disclosed herein, and when they are defined to be certain substituents in one instance, they can, in another instance, be defined as some other substituents.

At various places in the present specification, divalent linking substituents are described. It is specifically intended that each divalent linking substituent includes both the forward and backward forms of the linking substituent. For example, —NR(CR'R")$_n$-includes both —NR(CR'R")$_n$— and —(CR'R")$_n$NR—. Where the structure clearly requires a linking group, the Markush variables listed for that group are understood to be linking groups.

The term "n-membered," where n is an integer, typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

Throughout the definitions, the term "$C_n$-$C_m$" indicates a range that includes the endpoints, wherein n and m are integers and indicate the number of carbons. Examples include, without limitation, $C_1$-$C_4$, $C_1$-$C_6$, and the like.

The term "aliphatic" as used herein refers to a non-aromatic hydrocarbon group and includes branched and unbranched, alkyl, alkenyl, or alkynyl groups. As used herein, the term "$C_n$-$C_m$ alkyl," employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, teri-butyl, isobutyl, sec-butyl; higher homologs such as 2-methyl-I-butyl, n-pentyl, 3-pentyl, n-hexyl, 1,2,2-trimethylpropyl, heptyl, octyl, nonyl, decyl, dodecyl, tetradecyl, hexadecyl, eicosyl, tetracosyl, and the like. In various aspects, the alkyl group contains from 1 to 24 carbon atoms, from 1 to 12 carbon atoms, from 1 to 10 carbon atoms, from 1 to 8 carbon atoms, from 1 to 6 carbon atoms, from 1 to 4 carbon atoms, from 1 to 3 carbon atoms, or 1 to 2 carbon atoms. The alkyl group can also be substituted or unsubstituted. Throughout the specification, "alkyl" is generally used to refer to both unsubstituted alkyl groups and substituted alkyl groups; however, substituted alkyl groups are also specifically referred to herein by identifying the specific substituent(s) on the alkyl group. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

For example, the term "halogenated alkyl" specifically refers to an alkyl group that is substituted with one or more halides, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below and the like. When "alkyl" is used in one instance, and a specific term such as "alkylalcohol" is used in another, it is not meant to imply that the term "alkyl" does not also refer to specific terms such as "alkylalcohol" and the like.

As used herein, "$C_n$-$C_m$ alkenyl" refers to an alkyl group having one or more double carbon-carbon bonds and having n to m carbons. Example alkenyl groups include, but are not limited to, ethenyl, n-propenyl, isopropenyl, n-butenyl, seobutenyl, and the like. In various aspects, the alkenyl moiety contains 2 to 6, 2 to 4, or 2 to 3 carbon atoms. Asymmetric structures such as ($R^1R^2$)C=C($R^3R^4$) are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, cyano, silyl, sulfo-oxo, sulfonyl, sulfone, sulfoxide, thiol, thiol, or phosphonyl, as described below.

As used herein, "$C_n$-$C_m$ alkynyl" refers to an alkyl group having one or more triple carbon-carbon bonds and having n to m carbons. Exemplary alkynyl groups include, but are not limited to, ethynyl, propyn-1-yl, propyn-2-yl, and the like. In various aspects, the alkynyl moiety contains 2 to 6, 2 to 4, or 2 to 3 carbon atoms. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, cyano, silyl, sulfo-oxo, sulfonyl, sulfone, sulfoxide, thiol, or phosphonyl, as described below As used herein, the term "$C_n$-$C_m$ alkylene," employed alone or in combination with other terms, refers to a divalent alkyl linking group having n to m carbons. Examples of alkylene groups include, but are not limited to, ethan-1,2-diyl, propan-1,3-diyl, propan-1,2-diyl, butan-1,4-diyl, butan-1,3-diyl, butan-1,2-thyl, 2-methyl-propan-1,3-diyl, and the like. In various aspects, the alkylene moiety contains 2 to 6, 2 to 4, 2 to 3, 1 to 6, 1 to 4, or 1 to 2 carbon atoms.

As used herein, the term "$C_n$-$C_m$ alkoxy," employed alone or in combination with other terms, refers to a group of formula —O-alkyl, wherein the alkyl group has n to m carbons. Exemplary alkoxy groups include methoxy, ethoxy, propoxy (e.g., w-propoxy and isopropoxy), teri-butoxy, and the like. In various aspects, the alkyl group has 1 to 6, 1 to 4, or 1 to 3 carbon atoms.

The terms "amine" or "amino" as used herein are represented by the formula —$NR^1R^2$, where $R^1$ and $R^2$ can each be substitution group as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group described above. "Amido" is —C(O)$NR^1R^2$.

As used herein, the term "$C_n$-$C_m$ alkylamino" refers to a group of formula —NH(alkyl), wherein the alkyl group has n to m carbon atoms. In various aspects, the alkyl group has 1 to 6, 1 to 4, or 1 to 3 carbon atoms.

As used herein, the term "$C_n$-$C_m$ alkoxycarbonyl" refers to a group of formula —C(O)O-alkyl, wherein the alkyl group has n to m carbon atoms. In various aspects, the alkyl group has 1 to 6, 1 to 4, or 1 to 3 carbon atoms.

As used herein, the term "$C_n$-$C_m$ alkylcarbonyl" refers to a group of formula —C(O)-alkyl, wherein the alkyl group has n to m carbon atoms. In various aspects, the alkyl group has 1 to 6, 1 to 4, or 1 to 3 carbon atoms.

As used herein, the term "$C_n$-$C_m$ alkylcarbonylamino" refers to a group of formula —NHC(O)-alkyl, wherein the alkyl croup has n to m carbon atoms. In various aspects, the alkyl group has 1 to 6, 1 to 4, or 1 to 3 carbon atoms.

As used herein, the term "$C_n$-$C_m$ alkylsulfonylamino" refers to a group of formula —NHS(O)$_2$-alkyl, wherein the alkyl group has n to m carbon atoms. In various aspects, the alkyl group has 1 to 6, 1 to 4, or 1 to 3 carbon atoms.

The term "aldehyde" as used herein is represented by the formula —C(O)H. Throughout this specification, "C(O)" or "CO" is a shorthand notation for C=O, which is also referred to herein as a "carbonyl."

The term "carboxylic acid" as used herein is represented by the formula —C(O)OH. A "carboxylate" or "carboxyl" group as used herein is represented by the formula —C(O)O$^-$.

The term "ester" as used herein is represented by the formula —OC(O)$R^1$ or —C(O)O$R^1$, where $R^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $R^1OR^2$, where $R^1$ and $R^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $R^1C(O)R^2$, where $R^1$ and $R^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

As used herein, the term "aminosulfonyl" refers to a group of formula —S(O)$_2$NH$_2$.

As used herein, the term "$C_n$-$C_m$ alkylaminosulfonyl" refers to a group of formula —S(O)$_2$NH(alkyl), wherein the alkyl group has n to m carbon atoms. In various aspects, the alkyl group has 1 to 6, 1 to 4, or 1 to 3 carbon atoms.

As used herein, the term "di($C_n$-$C_m$ alkyl)aminosulfonyl" refers to a group of formula —S(O)$_2$N(alkyl)$_2$, wherein each alkyl group independently has n to m carbon atoms. In various aspects, each alkyl group has, independently, 1 to 6, 1 to 4, or 1 to 3 carbon atoms.

As used herein, the term "aminosulfonylamino" refers to a group of formula —NHS(O)$_2$NH$_2$.

As used herein, the term "$C_n$-$C_m$ alkylaminosulfonylamino" refers to a group of formula —NHS(O)$_2$NH(alkyl), wherein the alkyl group has n to m carbon atoms. In various aspects, the alkyl group has 1 to 6, 1 to 4, or 1 to 3 carbon atoms.

As used herein, the term "di($C_n$-$C_m$ alkyl)aminosulfonylamino" refers to a group of formula —NHS(O)$_2$N(alkyl)$_2$, wherein each alkyl group independently has n to m carbon atoms. In various aspects, each alkyl group has, independently, 1 to 6, 1 to 4, or 1 to 3 carbon atoms.

As used herein, the term "aminocarbonylamino," employed alone or in combination with other terms, refers to a group of formula —NHC(O)NH$_2$.

As used herein, the term "$C_n$-$C_m$ alkylaminocarbonylamino" refers to a group of formula —NHC(O)NH(alkyl), wherein the alkyl group has n to m carbon atoms. In various aspects, the alkyl group has 1 to 6, 1 to 4, or 1 to 3 carbon atoms.

As used herein, the term "di($C_n$-$C_m$ alkyl)aminocarbonylamino" refers to a group of formula —NHC(O)N(alkyl)$_2$, wherein each alkyl group independently has n to m carbon atoms. In various aspects, each alkyl group has, independently, 1 to 6, 1 to 4, or 1 to 3 carbon atoms.

As used herein, the term "$C_n$-$C_m$ alkylcarbamyl" refers to a group of formula —C(O)—NH(alkyl), wherein the alkyl group has n to m carbon atoms. In various aspects, the alkyl group has 1 to 6, 1 to 4, or 1 to 3 carbon atoms.

As used herein, the term "thio" refers to a group of formula —SH.

As used herein, the term "$C_n$-$C_m$ alkylthio" refers to a group of formula —S— alkyl, wherein the alkyl group has n to m carbon atoms. In various aspects, the alkyl group has 1 to 6, 1 to 4, or 1 to 3 carbon atoms.

As used herein, the term "$C_n$-$C_m$ alkylsulfmyl" refers to a group of formula —S(O)—alkyl, wherein the alkyl group has n to m carbon atoms. In various aspects, the alkyl group has 1 to 6, 1 to 4, or 1 to 3 carbon atoms.

As used herein, the term "$C_n$-$C_m$ alkylsulfonyl" refers to a group of formula —S(O)$_2$-alkyl, wherein the alkyl group has n to m carbon atoms. In various aspects, the alkyl group has 1 to 6, 1 to 4, or 1 to 3 carbon atoms.

As used herein, the term "carbamyl" to a group of formula —C(O)NH$_2$.

As used herein, the term "carbonyl," employed alone or in combination with other terms, refers to a —C(=O)— group, which may also be written as C(O).

As used herein, the term "carboxy" refers to a group of formula —C(O)OH.

As used herein, the term "($C_n$-$C_m$)($C_n$-$C_m$)amino" refers to a group of formula —N(alkyl)$_2$, wherein the two alkyl groups each has, independently, n to m carbon atoms. In various aspects, each alkyl group independently has 1 to 6, 1 to 4, or 1 to 3 carbon atoms.

As used herein, the term "di($C_n$-$C_m$-alkyl)carbamyl" refers to a group of formula —C(O)N(alkyl)$_2$, wherein the two alkyl groups each has, independently, n to m carbon atoms. In various aspects, each alkyl group independently has 1 to 6, 1 to 4, or 1 to 3 carbon atoms.

As used herein, "halogen" refers to F, Cl, Br, or I.

The term "hydroxyl" as used herein is represented by the formula —OH.

The term "cyano" as used herein is represented by the formula —CN.

The term "nitro" as used herein is represented by the formula —NO$_2$.

The term "phosphonyl" is used herein to refer to the phospho-oxo group represented by the formula —P(O)(OR$^1$)$_2$, where R$^1$ can be absent, hydrogen, an alkyl, alkenyl, alkynyl, aryl, heteroaryl, cycloalkyl, or cycloalkenyl.

The term "silyl" as used herein is represented by the formula —SiR$^1$R$^2$R$^3$, where R$^1$, R$^2$, and R$^3$ can be, independently, hydrogen, alkyl, halogenated alkyl, alkoxy, alkenyl, alkynyl, aryl, heteroaryl, cycloalkyl, cycloalkenyl, heterocycloalkyl, or heterocycloalkenyl group described above.

The term "sulfonyl" is used herein to refer to the sulfo-oxo group represented by the formula —S(O)$_2$R$^1$, where R$^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —S(O)$_2$NH—.

As used herein, "$C_n$-$C_m$ haloalkoxy" refers to a group of formula —O-haloalkyl having n to m carbon atoms. An example haloalkoxy group is OCF$_3$. In various aspects, the haloalkoxy group is fluorinated only. In various aspects, the alkyl group has 1 to 6, 1 to 4, or 1 to 3 carbon atoms.

As used herein, the term "$C_n$-$C_m$ haloalkyl," employed alone or in combination with other terms, refers to an alkyl group having from one halogen atom to 2s+1 halogen atoms, which may be the same or different, where "s" is the number of carbon atoms in the alkyl group, wherein the alkyl group has n to m carbon atoms. In various aspects, the haloalkyl group is fluorinated only. In various aspects, the alkyl group has 1 to 6, 1 to 4, or 1 to 3 carbon atoms.

As used herein, the term "amine base" refers to a mono-substituted amino group (i.e., primary amine base), di-substituted amino group (i.e., secondary amine base), or a tri-substituted amine group (i.e., tertiary amine base). Exemplary mono-substituted amine bases include methylamine, ethylamine, propylamine, butylamine, and the like. Examples of di-substituted amine bases include dimethylamine, diethylamine, dipropylamine, dibutylamine, pyrrolidine, piperidine, azepane, morpholine, and the like. In various aspects, the tertiary amine has the formula N(R')$_3$, wherein each R' is independently $C_1$-$C_6$ alkyl, 3-10 member cycloalkyl, 4-10 membered heterocycloalkyl, 1-10 membered heteroaryl, and 5-10 membered aryl, wherein the 3-10 member cycloalkyl, 4-10 membered heterocycloalkyl, 1-10 membered heteroaryl, and 5-10 membered aryl is optionally substituted by 1, 2, 3, 4, 5, or 6 C1-6 alkyl groups. Exemplary tertiary amine bases include trimethylamine, triethylamine, tripropylamine, triisopropylamine, tributylamine, tri-tert-butylamine, N,N-dimethylethanamine, N-ethyl-N-methylpropan-2-amine, N-ethyl-N-isopropylpropan-2-amine, morpholine, N-methylmorpholine, and the like. In various aspects, the term "tertiary amine base" refers to a group of formula N(R)$_3$, wherein each R is independently a linear or branched $C_{1-6}$ alkyl group.

As used herein, "cycloalkyl" refers to non-aromatic cyclic hydrocarbons, including cyclized alkyl and/or alkenyl groups. Cycloalkyl groups can include mono- or polycyclic (e.g., having 2, 3 or 4 fused rings) groups and spirocycles. Cycloalkyl groups can have 3, 4, 5, 6, 7, 8, 9, or 10 ring-forming carbons ($C_{3-10}$). Ring-forming carbon atoms of a cycloalkyl group can be optionally substituted by oxo or sulfido (e.g., C(O) or C(S)). Cycloalkyl groups also include cycloalkylidenes. Exemplary cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, and the like. In various aspects, cycloalkyl is cyclopropyl, cyclobutyl, cyclopentyl, cyclohexyl, cyclopentyl, or adamantyl. In various aspects, the cycloalkyl has 6-10 ring-forming carbon atoms. In various aspects, cycloalkyl is cyclohexyl or adamantyl. Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom, including a ring-forming atom of the fused aromatic ring.

As used herein, "heterocycloalkyl" refers to non-aromatic monocyclic or polycyclic heterocycles having one or more ring-forming heteroatoms selected from O, N, or S. Included in heterocycloalkyl are monocyclic 4-, 5-, 6-, and 7-membered heterocycloalkyl groups. Heterocycloalkyl groups can also include spirocycles. Exemplary heterocycloalkyl groups include pyrrolidin-2-one, 1,3-isoxazolidin-2-one, pyranyl, tetrahydropuran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by oxo or sulfido (e.g., C(O), S(O), C(S), or S(O)$_2$, etc.). The heterocycloalkyl group can be attached through a ring-forming carbon atom or a ring-forming heteroatom. In various aspects, the heterocycloalkyl group contains 0 to 3 double bonds. In various aspects, the heterocycloalkyl group contains 0 to 2 double bonds. Also included in the definition of heterocycloalkyl are moieties that have one or more aromatic rings fused (i.e., having a bond in common with) to the cycloalkyl ring, for example, benzo or thienyl derivatives of piperidine, morpholine, azepine, etc. A heterocycloalkyl group containing a fused aromatic ring can be attached through any ring-forming atom, including a ring-forming atom of the fused aromatic ring. In various aspects, the heterocycloalkyl has 4-10, 4-7, or 4-6 ring atoms with 1 or 2 heteroatoms independently selected from nitrogen, oxygen, or sulfur and having one or more oxidized ring members.

The term "cycloalkenyl," as used herein, is a non-aromatic carbon-based ring composed of at least three carbon atoms and containing at least one double bond, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above and is included within the meaning of the term "cycloalkenyl," where at least one of the carbon atoms of the ring is substituted with a heteroatom such as, but not limited to, nitrogen, oxygen, sulfur, or phosphorus.

The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, cyano, silyl, sulfo-oxo, sulfonyl, sulfone, sulfoxide, thiol, or phosphonyl, as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups, and one or more non-aryl groups.

As used herein, the term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl, and the like. In various aspects, aryl groups have from 6 to about 20 carbon atoms, from 6 to about 15 carbon atoms, or from 6 to about 10 carbon atoms. In various aspects, the aryl group is a substituted or unsubstituted phenyl.

As used herein, "heteroaryl" refers to a monocyclic or polycyclic aromatic heterocycle having at least one heteroatom ring member selected from sulfur, oxygen, phosphorus, and nitrogen. In various aspects, the heteroaryl ring has 1, 2, 3, or 4 heteroatom ring members independently selected from nitrogen, sulfur, and oxygen. In various aspects, any ring-forming N in a heteroaryl moiety can be an N-oxide. In various aspects, the heteroaryl has 5-10 ring atoms and 1, 2, 3 or 4 heteroatom ring members independently selected from nitrogen, sulfur, and oxygen. In various aspects, the heteroaryl has 5-6 ring atoms and 1 or 2 heteroatom ring members independently selected from nitrogen, sulfur, and oxygen. In various aspects, the heteroaryl is a five-membered or six-membered heteroaryl ring. A five-membered heteroaryl ring is a heteroaryl with a ring having five ring atoms wherein one or more (e.g., 1, 2, or 3) ring atoms are independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. A six-membered heteroaryl ring is a heteroaryl with a ring having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl, and pyridazinyl.

The aryl or heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, cyano, silyl, sulfo-oxo, sulfonyl, sulfone, sulfoxide, thiol, or phosphonyl, as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

At certain places, the definitions or aspects refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas an azetidin-3-yl ring is attached at the 3-position.

As used herein, the term "electron withdrawing group" (EWG), employed alone or in combination with other terms, refers to an atom or group of atoms substituted onto a π-system (e.g., substituted onto an aryl or heteroaryl ring) that draws electron density away from the π-system through induction (e.g., withdrawing electron density about a σ-bond) or resonance (e.g., withdrawing electron density about a π-bond or π-system). Example electron withdrawing groups include, but are not limited to, halo groups (e.g., fluoro, chloro, bromo, iodo), nitriles (e.g., —CN), carbonyl groups (e.g., aldehydes, ketones, carboxylic acids, acid chlorides, esters, and the like), nitro groups (e.g., —NO$_2$), haloalkyl groups (e.g., —CH$_2$F, —CHF$_2$, —CF$_3$, and the like), alkenyl groups (e.g., vinyl), alkynyl groups (e.g., ethynyl), sulfonyl groups (e.g., S(O)R, S(O)$_2$R), sulfonate groups (e.g., —SO$_3$H), and sulfonamide groups (e.g., S(O)N(R)$_2$, S(O)$_2$N(R)=). In various aspects, the electron withdrawing group is selected from the group consisting of halo, C$_2$-C$_6$ alkenyl, C$_2$-C$_6$ alkynyl, C$_1$-C$_3$ haloalkyl, ON, NO$_2$, O(=O)OR$^{al}$, O(=O)R$^{bl}$, C(=O)NR$^{cl}$R$^{dl}$, C(=O)SR$^{el}$, —NR$^{cl}$S(O)R$^{el}$, —NR$^{cl}$S(O)$_2$R$^{el}$, S(=O)R$^{el}$, S(=O)$_2$R$^{el}$, S(=O)NR$^{cl}$R$^{dl}$, S(=O)$_2$NR$^{cl}$R$^{dl}$, and P(O)(OR$^{al}$)$_2$. In various aspects, the electron withdrawing group is selected from the group consisting of C(=O)OR$^{el}$, C(=O)R$^{bl}$, O(=O)NR$^{cl}$R$^{dl}$, C(=O)SR$^{el}$, S(=O)R$^{el}$, S(=O)$_2$R$^{el}$, S(=O)NR$^{cl}$R$^{dl}$, and S(=O)$_2$NR$^{cl}$R$^{dl}$. In various aspects, the electron withdrawing group is C(=O)OR$^{al}$. In various aspects, the electron withdrawing group is O(=O)OR$^{al}$, wherein R$^{al}$, R$^{cl}$, R$^{dl}$, and R$^{el}$ are independently selected at each occurrence from alkyl, alkenyl, alkynyl, cycloalkyl, cycloalkenyl, heterocycloalkyl, aryl, or heteroaryl, each of which R$^{al}$, R$^{bl}$, R$^{cl}$, R$^{dl}$, or R$^{el}$ may be optionally substituted with one or more substituents as described herein.

"R$^1$," "R$^2$," "R$^3$," "R$^n$," etc., where n is some integer, as used herein can, independently, possess one or more of the groups listed above. For example, if R$^1$ is a straight chain alkyl group, one of the hydrogen atoms of the alkyl group can optionally be substituted with a hydroxyl group, an alkoxy group, an amine group, an alkyl group, a halide, and the like. Depending upon the groups that are selected, a first group can be incorporated within the second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

The term "protecting groups" as used herein refers to any molecular framework that can temporarily mask a specific functional group to block its reactivity under reaction conditions when modifications are needed elsewhere in the molecule. It is understood that the protecting groups can comprise any molecular framework that can be selectively introduced, stable, resistant to reagents employed in subsequent reaction steps in which the group is masked (protected) is desired to remain deactivated (protected). It is further understood that the protecting groups used herein can be selectively removed under mild conditions when their protection is no longer required. In some exemplary and non-limiting aspects, the protecting groups can comprise ethers, silyls, acetals, ketals, esters, carbamates, and the like.

In still further exemplary aspects described herein, the protecting group can comprise a benzyl group.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

Dashed lines in a chemical structure are used to indicate that a bond may be present or absent or that it may be a delocalized bond between the indicated atoms.

As used herein, substantially pure means sufficiently homogeneous to appear free of readily detectable impurities as determined by standard methods of analysis, such as thin-layer chromatography (TLC), nuclear magnetic resonance (NMR), gel electrophoresis, high-performance liquid chromatography (HPLC) and mass spectrometry (MS), gas-chromatography mass spectrometry (GC-MS), and similar, used by those of skill in the art to assess such purity, or sufficiently pure such that further purification would not detectably alter the physical and chemical properties, such as enzymatic and biological activities, of the substance. Both traditional and modern methods for purification of the compounds to produce substantially chemically pure compounds are known to those of skill in the art. A substantially chemically pure compound can, however, be a mixture of stereoisomers.

Preparation of the compounds described herein can involve a reaction in the presence of an acid or a base. Example acids can be inorganic or organic acids and include, but are not limited to, strong and weak acids. Example acids include, but are not limited to, hydrochloric acid, hydrobromic acid, sulfuric acid, phosphoric acid, p-toluenesulfonic acid, 4-nitrobenzoic acid, methanesulfonic acid, benzenesulfonic acid, trifluoroacetic acid, and nitric acid. Example weak acids include, but are not limited to, acetic acid, propionic acid, butanoic acid, benzoic acid, tartaric acid, pentanoic acid, hexanoic acid, heptanoic acid, octanoic acid, nonanoic acid, and decanoic acid. Examples include, without limitation, lithium hydroxide, sodium hydroxide, potassium hydroxide, lithium carbonate, sodium carbonate, potassium carbonate, sodium bicarbonate, and amine bases. Example strong bases include, but are not limited to, hydroxide, alkoxides, metal amides, metal hydrides, metal dialkylamides, and arylamines, wherein; alkoxides include lithium, sodium and potassium salts of methyl, ethyl and t-butyl oxides; metal amides include sodium amide, potassium amide, and lithium amide; metal hydrides include sodium hydride, potassium hydride, and lithium hydride; and metal dialkylamides include lithium, sodium, and potassium salts of methyl, ethyl, n-propyl, iso-propyl, n-butyl, t-butyl, trimethylsilyl, and cyclohexyl substituted amides (e.g., lithium N-isopropylcyclohexylamide).

The following abbreviations may be used herein: AcOH (acetic acid); aq. (aqueous); atm. (atmosphere(s)); $Br_2$ (bromine); Bn (benzyl); calc. (calculated); d (doublet); dd (doublet of doublets); DCM (dichloromethane); DMF (N,N-dimethylformamide); Et (ethyl); $Et_2O$ (diethyl ether); EtOAc (ethyl acetate); EtOH (ethanol); EWG (electron withdrawing group); g (gram(s)); h (hour(s)); HCl (hydrochloric acid/hydrogen chloride); HPLC (high performance liquid chromatography); $H_2SO_4$ (sulfuric acid); Hz (hertz); (iodine); IPA (isopropyl alcohol); J (coupling constant); KOH (potassium hydroxide); $K_3PO_4$ (potassium phosphate); LCMS (liquid chromatography-mass spectrometry); GC (gas chromatography), LiICA (lithium N-isopropylcyclohexylamide); m (multiplet); M (molar); MS (Mass spectrometry); Me (methyl); MeCN (acetonitrile); MeOH (methanol); mg (milligram(s)); min. (minutes(s)); mL (milliliter(s)); mmol (millimole(s)); N (normal); $NaBH_4CN$ (sodium cyanoborohydride); NHP (N-heterocyclic phosphine); NHP-Cl (N-heterocyclic phosphine chloride); $Na_2CO_3$ (sodium carbonate); $NaHCO_3$ (sodium bicarbonate); NaOH (sodium hydroxide); $Na_2SO_4$ (sodium sulfate); nM (nanomolar NMR (nuclear magnetic resonance spectroscopy); PCP (trichlorophosphine); PMP (4-methoxyphenyl); RP-HPLC (reverse phase high performance liquid chromatography); t (triplet or tertiary); t-Bu (teri-butyl); TEA (triethylamine); TFA (trifluoroacetic acid); THF (tetrahydrofuran); TLC (thin layer chromatography); μg (microgram(s)); μL (microliter(s)); μM (micromolar); wt % (weight percent).

Reference will now be made in detail to specific aspects of the disclosed materials, compounds, compositions, articles, and methods, examples of which are illustrated in the accompanying Examples.

Materials and Compositions

Disclosed herein are materials, compounds, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, suppose a composition is disclosed, and a number of modifications that can be made to a number of components of the composition are discussed. In that case, each and every combination and permutation that are possible are specifically contemplated unless specifically indicated to the contrary. Thus, if a class of components A, B, and C are disclosed and a class of components D, E, and F and an example of a combination composition A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure, including, but not limited to, steps in methods of making and using the disclosed compositions. Thus, if there are a variety of additional steps that can be performed, it is understood that each of these additional steps can be performed with any specific aspect or combination of aspects of the disclosed methods and that each such combination is specifically contemplated and should be considered disclosed.

Imidazole-Amine Compounds

The compounds disclosed herein refer to imidazole-amine compounds or imidazole tethered to amine compounds. It is understood that these two terms can be used interchangeably.

In still further aspects, disclosed herein are imidazole-amine compounds of formula (I):

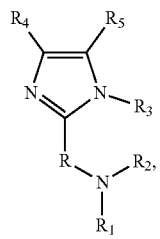

(I)

wherein

R is selected from null, $C_{1-20}$ alkyl, $C_{2-20}$ alkenyl, $C_1$-$C_{20}$ alkoxy, $C_{2-20}$ alkynyl, $C_{1-20}$ heteroalkyl, $C_{2-20}$ heteroalkenyl, $C_{2-20}$ heteroalkynyl, $C_6$-$C_{14}$ aryl, $C_1$-$C_{13}$ heteroaryl, $C_6$-$C_{14}$ aryloxy; wherein R is optionally substituted with $C_1$-$C_{20}$ alkyl, $C_1$-$C_{20}$ alkoxy, $C_2$-$C_{20}$ alkenyl, $C_2$-$C_{20}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl; and $R_1$ and $R_2$ are, independent of one another, hydrogen, $C_{1-20}$ alkyl, $C_{2-20}$ alkenyl, $C_1$-$C_{20}$ alkoxy, $C_{2-20}$ alkynyl, $C_{1-20}$ heteroalkyl, $C_{2-20}$ heteroalkenyl, $C_{2-20}$ heteroalkynyl, $C_6$-$C_{14}$ aryl, $C_1$-$C_{13}$ heteroaryl, $C_6$-$C_{14}$ aryloxy, carbonyl, ester, ether, halide, carboxyl, hydroxy, nitro, cyano, silyl, sulfo-oxo, sulfonyl, sulfone, sulfoxide, thiol, or phosphonyl; wherein each $R_1$ or $R_2$ independent of each other is optionally substituted with $C_1$-$C_{20}$ alkyl, $C_1$-$C_{20}$ alkoxy, $C_2$-$C_{20}$ alkenyl, $C_2$-$C_{20}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl;

$R_3$ is selected from hydrogen, $C_1$-$C_{10}$ alkyl, $C_1$-$C_{10}$ alkoxy, $C_6$-$C_{14}$ aryl, $C_1$-$C_{13}$ heteroaryl, $C_6$-$C_{14}$ aryloxy, wherein $R_3$ is optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl;

$R_4$ and $R_5$ are each independent of the other, selected from hydrogen, $C_{1-20}$ alkyl, $C_{2-20}$ alkenyl, $C_1$-$C_{20}$ alkoxy, $C_{2-20}$ alkynyl, $C_{1-20}$ heteroalkyl, $C_{2-20}$ heteroalkenyl, $C_{2-20}$ heteroalkynyl, $C_6$-$C_{14}$ aryl, $C_1$-$C_{13}$ heteroaryl, $C_6$-$C_{14}$ aryloxy, carbonyl, ester, ether, halide, carboxyl, hydroxy, nitro, cyano, silyl, sulfo-oxo, sulfonyl, sulfone, sulfoxide, thiol, or phosphonyl; wherein each $R_1$ or $R_2$ independent of each other is optionally substituted with $C_1$-$C_{20}$ alkyl, $C_1$-$C_{20}$ alkoxy, $C_2$-$C_{20}$ alkenyl, $C_2$-$C_{20}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl; or wherein $R_4$ and $R_5$ together form a 6 membered aromatic ring containing 6 carbon atoms.

In still further exemplary and unlimiting aspects, the R can be selected from —$CH_2$—, —$CH(CH_3)$—, —$C(CH_3)_2$—, —$CH_2CH_2$—, —$CH_2CH(CH_3)$—, —$CH_2C(CH_3)_2$—, —$CH_2CH_2CH_2$, —$CH_2CH_2CH(CH_3)$—, or —$CH_2CH_2C(CH_3)_2$—.

In yet further aspects, the imidazole compounds used herein can be selected from

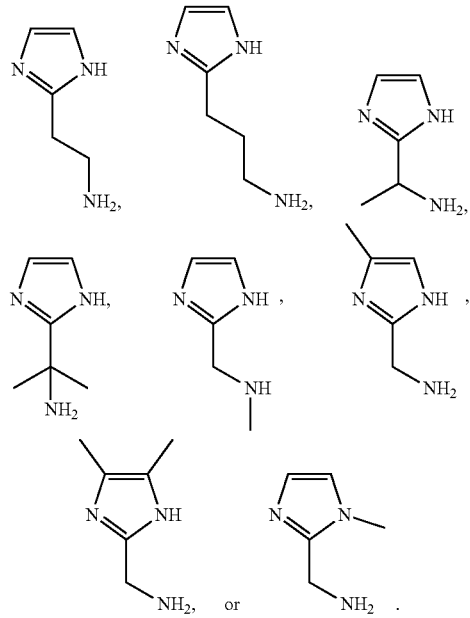

In certain aspects, any of the disclosed herein imidazole compounds can be utilized. In yet other aspects, a combination of various imidazole compounds can be used for the described purposes.

Any of the imidazole compounds disclosed herein or their combination can be used to form a solution. In such aspects, the solution can comprise any of the disclosed above imidazole compounds or their combination and a solvent. In some exemplary aspects, the solvent can comprise one or more of water, tetrahydrofuran, dichloromethane, acetonitrile, toluene, dimethyl sulfoxide, pyridine, dimethylformamide, dioxane, glycol solvents, methanol, ethanol, propanol, butanol, ethyl acetate, methyl ethyl ketone, or acetone. In still further exemplary and unlimiting aspects, the solvent comprises water.

In still further aspects, the solutions disclosed herein can be configured to absorb one or more volatile compounds comprising carbon dioxide, hydrogen sulfide, sulfur dioxide, nitrogen oxide, nitrogen dioxide, carbonyl sulfide, carbon disulfide, or mixtures thereof. It is understood that these volatile compounds can be absorbed from a gas feed, or liquid feed, or fluid feed, or any combination thereof.

In yet further aspects, the compounds disclosed herein are useful for reducing volatile compounds, such as carbon dioxide ($CO_2$), carbon monoxide (CO), sulfur dioxide ($SO_2$), hydrogen sulfide ($H_2S$), nitrogen oxide (NO), nitrogen dioxide ($NO_2$), carbonyl sulfide (COS), and carbon disulfide ($CS_2$), mercaptans, $H_2O$, $O_2$, $H_2$, $N_2$, $C_1$-$C_8$ hydrocarbons (e.g., methane and propane), volatile organic compounds, and mixtures of these and other volatile compounds from gas streams and liquid streams.

The inventors have discovered that compared to the existing flue gas $CO_2$ capture technology, the disclosed herein compounds have enhanced thermal and chemical stability and are capable of absorbing a greater amount of volatile compounds, such as for example, carbon dioxide. However, it is also understood that the disclosed compounds are capable of absorbing a greater amount of other volatile compounds when compared with the existing technologies.

In still further aspects, the compounds disclosed herein are tunable and are configured to be adopted to optimal treatment of the gas or liquid by tuning the functionalization and a type of amine bonded to the imidazole.

In still further aspects, the imidazole compounds disclosed herein can be non-ionic compounds under neutral compounds (i.e., the imidazoles do not contain a charge under neutral conditions). Neutral conditions include conditions where no proton is available to react with the imidazole tethered to an amine (i.e., to protonate the imidazole tethered to an amine). Protons can be present, but the conditions of the system, including the basicity of the imidazole tethered to an amine, are such that no significant amount of protonation of the imidazole tethered to an amine occurs, i.e., the conditions do not produce imidazolium ion. Neutral conditions for the imidazole tethered to an amine include conditions where the pH of the system is from about 6.7 to about 7.3. In some examples, the pH of the system can be about 6.7, about 6.8, about 6.9, about 7.0, about 7.1, about 7.2, about 7.3, or the like, where any of the stated values can form an upper or lower endpoint of a range. The term "neutral conditions" is used herein relative to the specific imidazole, thus this term means conditions wherein the imidazole is not protonated (i.e., made cationic). For example, the pH of the system can be from about 6.8 to about 7.2, or from about 6.9 to about 7.1. Further, the imidazole compounds described herein are not components of an ionic liquid (i.e., liquids that contain ions under all conditions).

In still further aspects, the solutions disclosed herein are not ionic liquids. For example, the combination of an imidazole tethered to an amine (or imidazole-amine compound) is not a low melting salt. Upon addition of an acidic gas (e.g., $CO_2$, $H_2S$, etc.), the system comprising the disclosed herein solution can contain a charge. Further, the systems described herein can be distilled, whereas ionic liquids do not have this capability. The systems disclosed herein can be neat (i.e., can be composed of the imidazole tethered to an amine without any additional solvent) or can be dissolved or dispersed in one or more additional solvents. In some aspects, the system is a neat system comprised primarily of an imidazole tethered to an amine. Systems comprised primarily of the imidazole tethered to an amine can contain about 3 wt. % or less of impurities (i.e., the system contains about 97 wt. % or higher, about 98 wt. % or higher, or about 99 wt. % or higher imidazole tethered to an amine based on the weight of the system).

In some aspects, the system is a neat system composed of a mixture of an imidazole tethered to an amine. The mixture of the imidazole tethered to an amine (or imidazole-amine compound) can comprise any of the disclosed herein compounds. The system can have low volatility, low viscosity, and high $CO_2$ capacity, for example. The properties of the system can be altered by a percentage of the imidazole tethered to an amine in a solvent.

In still further aspects, the imidazole of formula (I), as described herein, is configured to absorbs carbon dioxide, for example, in a ratio of 1:3. In certain exemplary aspects, an exemplary imidazole of formula (I) having a molecular weight of about 96 g/mol can absorb up to 3 molecules of carbon dioxide.

In certain aspects, the imidazole amine compound can be present in a specific system in any amount from greater than 0 wt % to 100% of the solution. In yet other aspects, the imidazole compounds described herein can be present in any amount from greater than 0 wt % to less than 100 wt %, including exemplary values of about 1 wt %, about 2 wt %, about 3 wt %, about 4 wt %, about 5 wt %, about 6 wt %, about 7 wt %, about 8 wt %, about 9 wt %, about 10 wt %, about 11 wt %, about 12 wt %, about 13 wt %, about 14 wt %, about 15 wt %, about 16 wt %, about 17 wt %, about 18 wt %, about 19 wt %, about 20 wt %, about 21 wt %, about 22 wt %, about 23 wt %, about 24 wt %, about 25 wt %, about 26 wt %, about 27 wt %, about 28 wt %, about 29 wt %, about 30 wt %, about 31 wt %, about 32 wt %, about 33 wt %, about 34 wt %, about 35 wt %, about 36 wt %, about 37 wt %, about 38 wt %, about 39 wt %, about 40 wt %, about 41 wt %, about 42 wt %, about 43 wt %, about 44 wt %, about 45 wt %, about 46 wt %, about 47 wt %, about 48 wt %, about 49 wt %, about 50 wt %, about 51 wt %, about 52 wt %, about 53 wt %, about 54 wt %, about 55 wt %, about 56 wt %, about 57 wt %, about 58 wt %, about 59 wt %, about 60 wt %, about 61 wt %, about 62 wt %, about 63 wt %, about 64 wt %, about 65 wt %, about 66 wt %, about 67 wt %, about 68 wt %, about 69 wt %, about 70 wt %, about 71 wt %, about 72 wt %, about 73 wt %, about 74 wt %, about 75 wt %, about 76 wt %, about 77 wt %, about 78 wt %, about 79 wt %, about 80 wt %, about 81 wt %, about 82 wt %, about 83 wt %, about 84 wt %, about 85 wt %, about 86 wt %, about 87 wt %, about 88 wt %, about 89 wt %, about 90 wt %, about 91 wt %, about 92 wt %, about 93 wt %, about 94 wt %, about 95 wt %, about 96 wt %, about 97 wt %, about 98 wt %, about 99 wt %, and about 99.9 wt %. In further examples, the imidazole tethered to an amine can comprise from 1% to 99%, 10% to 90%, 20% to 80%, 30% to 70%, 40% to 60%, or 50% by weight of the solution. In yet other aspects, the imidazole-amine compound can be present in a specific system in any amount from about 10 wt % to about 90% of the solution. For example, the imidazole tethered to an amine can comprise 40% of the solution. In other examples, the imidazole tethered to an amine can comprise 60% of the solution.

The systems described herein are substantially free from amines, not tethered to an imidazole (e.g., free amines). By substantially free is meant that free amines are present at less than about 3%, 2%, 1%, 0.9%, 0.8%, 0.7%, 0.6%, 0.5%, 0.4%, 0.3%, 0.2%, 0.1%, 0.001%, 0.0001% by weight of the system.

As described above, the systems described herein can be dissolved or dispersed in one or more additional solvents. For example, the imidazole tethered to an amine can be mixed with a solvent such as water, tetrahydrofuran (THF), dichloromethane, acetonitrile, toluene, dimethyl sulfoxide (DMSO), pyridine, dimethylformamide, dioxane, glycol solvents, methanol, ethanol, propanol, butanol, ethyl acetate, methyl ethyl ketone, acetone, and the like to provide a system. In these examples, the imidazole tethered to an amine can comprise from about 0.1% to about 99.9% of the system. For example, the imidazole tethered to an amine can comprise from about 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, or 1% by weight of the system, where any of the stated values can form an upper or lower endpoint of a range. In further examples, the imidazole tethered to an amine can comprise from 1% to 99%, 10% to 90%, 20% to 80%, 30% to 70%, 40% to 60%, or 50% by weight of the system.

The systems described herein are substantially free from volatile organic compounds. By substantially free is meant that volatile organic compounds are present at less than about 3%, 2%, 1%, 0.9%, 0.8%, 0.7%, 0.6%, 0.5%, 0.4%, 0.3%, 0.2%, 0.1%, 0.001%, or 0.0001% by weight of the system.

Methods of Using Imidazole Compounds

The systems disclosed herein disclosed herein can be used to capture volatile compounds from a stream. The systems make use of a composition where an imidazole is tethered to an amine. By tethering an amine functional group to an imidazole through a covalent bond, the vapor pressure of the amine can be lowered. Additionally, these compounds can be prepared with commodity chemicals, which can result in lower system costs.

The methods for reducing volatile compounds from streams (e.g., gas streams or liquid streams) can be similar to those described in Bara et al. U.S. Published Patent Application No. 20090291874 A1, U.S. Pat. Nos. 8,506,914, 8,741,246, or 10,350,544 contents of which are incorporated by reference in their whole entirety herein.

As used herein, volatile compounds can include to undesirable gaseous components found in a source and having a molecular weight lower than 150 g/mol. For example, the volatile compounds can have a molecular weight lower than 140 g/mol, 130 g/mol, 120 g/mol, 110 g/mol, 100 g/mol, 90 g/mol, 80 g/mol, 70 g/mol, 60 g/mol, 50 g/mol, 40 g/mol, 30 g/mol, 20 g/mol, or the like, where any of the stated values can form an upper or lower endpoint of a range. Examples of volatile compounds include $CO_2$, CO, COS, $H_2S$, $SO_2$, NO, $N_2O$, mercaptans, $H_2O$, $O_2$, $H_2$, $N_2$, $C_1$-$C_8$ hydrocarbons (e.g., methane and propane), volatile organic compounds, and mixtures of these.

The method for reducing a volatile compound from a stream can include contacting the stream with an effective amount of the compounds as described herein. In some aspects, the system comprises an imidazole tethered to an amine and a solvent. For example, volatile compounds from a gas stream (e.g., a natural gas stream or a flue gas stream) can be reduced according to this method.

In some specific aspects, the method of reducing one or more volatile compounds from a stream comprises: contacting a stream with a solution comprising an imidazole having formula (I) and a solvent,

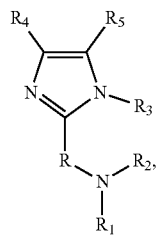

(I)

wherein
R is selected from null, $C_{1-20}$ alkyl, $C_{2-20}$ alkenyl, $C_{1-20}$ alkoxy, $C_{2-20}$ alkynyl, $C_{1-20}$ heteroalkyl, $C_{2-20}$ heteroalkenyl, $C_{2-20}$ heteroalkynyl, $C_6$-$C_{14}$ aryl, $C_1$-$C_{13}$ heteroaryl, $C_6$-$C_{14}$ aryloxy; wherein R is optionally substituted with $C_1$-$C_{20}$ alkyl, $C_1$-$C_{20}$ alkoxy, $C_2$-$C_{20}$ alkenyl, $C_2$-$C_{20}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl; and $R_1$ and $R_2$ are, independent of one another, hydrogen, $C_{1-20}$ alkyl, $C_{2-20}$ alkenyl, $C_{1-20}$ alkoxy, $C_{2-20}$ alkynyl, $C_{1-20}$ heteroalkyl, $C_{2-20}$ heteroalkenyl, $C_{2-20}$ heteroalkynyl, $C_6$-$C_{14}$ aryl, $C_1$-$C_{13}$ heteroaryl, $C_6$-$C_{14}$ aryloxy, carbonyl, ester, ether, halide, carboxyl, hydroxy, nitro, cyano, silyl, sulfo-oxo, sulfonyl, sulfone, sulfoxide, thiol, or phosphonyl; wherein each $R_1$ or $R_2$ independent of each other is optionally substituted with $C_1$-$C_{20}$ alkyl, $C_1$-$C_{20}$ alkoxy, $C_2$-$C_{20}$ alkenyl, $C_2$-$C_{20}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl;

$R_3$ is selected from hydrogen, $C_1$-$C_{10}$ alkyl, $C_1$-$C_{10}$ alkoxy, $C_6$-$C_{14}$ aryl, $C_1$-$C_{13}$ heteroaryl, $C_6$-$C_{14}$ aryloxy, wherein $R_3$ is optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl;

$R_4$ and $R_5$ are each independent of the other, selected from hydrogen, $C_{1-20}$ alkyl, $C_{2-20}$ alkenyl, $C_{1-20}$ alkoxy, $C_{2-20}$ alkynyl, $C_{1-20}$ heteroalkyl, $C_{2-20}$ heteroalkenyl, $C_{2-20}$ heteroalkynyl, $C_6$-$C_{14}$ aryl, $C_1$-$C_{13}$ heteroaryl, $C_6$-$C_{14}$ aryloxy, carbonyl, ester, ether, halide, carboxyl, hydroxy, nitro, cyano, silyl, sulfo-oxo, sulfonyl, sulfone, sulfoxide, thiol, or phosphonyl; wherein each $R_1$ or $R_2$ independent of each other is optionally substituted with $C_1$-$C_{20}$ alkyl, $C_1$-$C_{20}$ alkoxy, $C_2$-$C_{20}$ alkenyl, $C_2$-$C_{20}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl; or wherein $R_4$ and $R_5$ together form a 6 membered aromatic ring containing 6 carbon atoms.

In yet further exemplary aspects, R can be selected from —$CH_2$—, —$CH(CH_3)$—, —$C(CH_3)_2$—, —$CH_2CH_2$—, —$CH_2CH(CH_3)$—, —$CH_2C(CH_3)_2$—, —$CH_2CH_2CH_2$, —$CH_2CH_2CH(CH_3)$—, or —$CH_2CH_2C(CH_3)_2$—.

In still further exemplary and unlimiting aspects, the imidazole of formula (I) is selected from

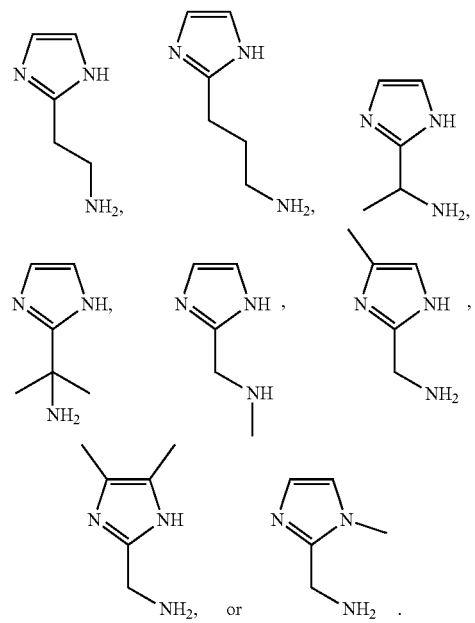

In still other aspects, the imidazole of formula (I), as described herein, can absorb the one or more volatile compounds. In yet further aspects, the imidazole of formula (I) can form at least one complex with the one or more volatile compounds.

In still further aspects, the methods can further comprise removing the at least one complex from the gas stream.

It is understood that the imidazole-amine compounds used in the disclosed methods can be present in any amount in the solution as described above.

In yet further aspects, the imidazole-amine compound can absorb volatile compounds such as carbon dioxide, for example, in a ratio of 1:3.

Further described herein is a method for sweetening a natural gas feed stream. The method comprises a) contacting the natural gas feed stream with a solution comprising an imidazole of formula (I) and a solvent,

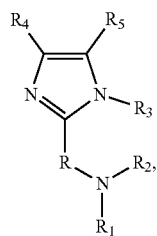
(I)

wherein

R is selected from null, $C_{1-20}$ alkyl, $C_{2-20}$ alkenyl, $C_{1-20}$ alkoxy, $C_{2-20}$ alkynyl, $C_{1-20}$ heteroalkyl, $C_{2-20}$ heteroalkenyl, $C_{2-20}$ heteroalkynyl, $C_6$-$C_{14}$ aryl, $C_1$-$C_{13}$ heteroaryl, $C_6$-$C_{14}$ aryloxy; wherein R is optionally substituted with $C_1$-$C_{20}$ alkyl, $C_1$-$C_{20}$ alkoxy, $C_2$-$C_{20}$ alkenyl, $C_2$-$C_{20}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl; and $R_1$ and $R_2$ are, independent of one another, hydrogen, $C_{1-20}$ alkyl, $C_{2-20}$ alkenyl, $C_{1-20}$ alkoxy, $C_{2-20}$ alkynyl, $C_{1-20}$ heteroalkyl, $C_{2-20}$ heteroalkenyl, $C_{2-20}$ heteroalkynyl, $C_6$-$C_{14}$ aryl, $C_1$-$C_{13}$ heteroaryl, $C_6$-$C_{14}$ aryloxy, carbonyl, ester, ether, halide, carboxyl, hydroxy, nitro, cyano, silyl, sulfo-oxo, sulfonyl, sulfone, sulfoxide, thiol, or phosphonyl; wherein each $R_1$ or $R_2$ independent of each other is optionally substituted with $C_1$-$C_{20}$ alkyl, $C_1$-$C_{20}$ alkoxy, $C_2$-$C_{20}$ alkenyl, $C_2$-$C_{20}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl;

$R_3$ is selected from hydrogen, $C_1$-$C_{10}$ alkyl, $C_1$-$C_{10}$ alkoxy, $C_6$-$C_{14}$ aryl, $C_1$-$C_{13}$ heteroaryl, $C_6$-$C_{14}$ aryloxy, wherein $R_3$ is optionally substituted with $C_1$-$C_{10}$ alkyl, alkoxy, $C_2$-$C_{10}$ alkenyl, $C_2$-$C_{10}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl;

$R_4$ and $R_5$ are each independent of the other, selected from hydrogen, $C_{1-20}$ alkyl, $C_{2-20}$ alkenyl, $C_{1-20}$ alkoxy, $C_{2-20}$ alkynyl, $C_{1-20}$ heteroalkyl, $C_{2-20}$ heteroalkenyl, $C_{2-20}$ heteroalkynyl, $C_6$-$C_{14}$ aryl, $C_1$-$C_{13}$ heteroaryl, $C_6$-$C_{14}$ aryloxy, carbonyl, ester, ether, halide, carboxyl, hydroxy, nitro, cyano, silyl, sulfo-oxo, sulfonyl, sulfone, sulfoxide, thiol, or phosphonyl; wherein each $R_1$ or $R_2$ independent of each other is optionally substituted with $C_1$-$C_{20}$ alkyl, $C_1$-$C_{20}$ alkoxy, $C_2$-$C_{20}$ alkenyl, $C_2$-$C_{20}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl; or wherein $R_4$ and $R_5$ together form a 6 membered aromatic ring containing 6 carbon atoms;

b) forming a purified gas feed stream and a gas-rich solution; and c) separating the purified gas feed stream and the gas-rich solution.

In certain exemplary and unlimiting aspects, in step b) of the disclosed herein methods, the one or more volatile compounds are transferred to the gas-rich solution. In yet other aspects, the one or more volatile compounds form at least one complex with the imidazole-amine compounds as disclosed herein.

Optionally, the natural gas feed stream can be contacted with a second solution, as described herein. The second solution can also comprise any of the disclosed herein imidazole-amine compounds and solvents. The contacting of the natural gas feed stream with the second solution can be performed simultaneously as the contacting with the first solution (i.e., the gas feed stream can be contacted with both the first and second solutions) or can be performed sequentially (i.e., the gas feed stream can be contacted with the second solution after the gas feed stream has been contacted with the first solution; or the gas feed stream can be contacted with the second solution before contact with the first solution). The purified natural gas feed stream can then be separated from the gas-rich solution. In some aspects, the volatile compounds are reduced from the gas-rich system to regenerate the system. The system can be regenerated by heating or pressurizing the gas-rich system.

In still further aspects, the disclosed herein methods can be performed in a continuous mode or a batch mode.

Methods of Making Imidazole-Amine Compounds

In certain aspects, also disclosed herein are methods of making an imidazole compound of formula (II) comprising:
a) oxidizing a compound having a general formula of (III)

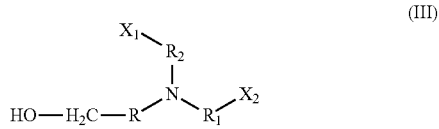
(III)

to form an aldehyde of general formula (IV):

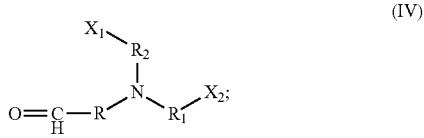
(IV)

b) reacting the aldehyde of formula (IV) with a dialdehyde compound of formula (V)

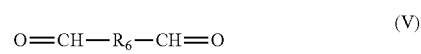
(V)

and an ammonium salt to form a compound of general formula (VI):

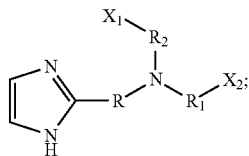

and c) deprotecting the compound of formula (VI) to form the compound of formula (II):

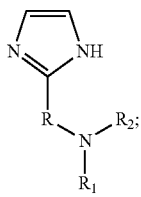

wherein

R is selected from null, $C_{1-20}$ alkyl, $C_{2-20}$ alkenyl, $C_{1-20}$ alkoxy, $C_{2-20}$ alkynyl, $C_{1-20}$ heteroalkyl, $C_{2-20}$ heteroalkenyl, $C_{2-20}$ heteroalkynyl, $C_6$-$C_{14}$ aryl, $C_1$-$C_{13}$ heteroaryl, $C_6$-$C_{14}$ aryloxy; wherein R is optionally substituted with $C_1$-$C_{20}$ alkyl, $C_1$-$C_{20}$ alkoxy, $C_2$-$C_{20}$ alkenyl, $C_2$-$C_{20}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl; and $R_1$ and $R_2$ are, independent of one another, hydrogen, $C_{1-20}$ alkyl, $C_{2-20}$ alkenyl, $C_1$-$C_{20}$ alkoxy, $C_{2-20}$ alkynyl, $C_{1-20}$ heteroalkyl, $C_{2-20}$ heteroalkenyl, $C_{2-20}$ heteroalkynyl, $C_6$-$C_{14}$ aryl, $C_1$-$C_{13}$ heteroaryl, $C_6$-$C_{14}$ aryloxy, carbonyl, ester, ether, halide, carboxyl, hydroxy, nitro, cyano, silyl, sulfo-oxo, sulfonyl, sulfone, sulfoxide, thiol, or phosphonyl; wherein each $R_1$ or $R_2$ independent of each other is optionally substituted with $C_1$-$C_{20}$ alkyl, $C_1$-$C_{20}$ alkoxy, $C_2$-$C_{20}$ alkenyl, $C_2$-$C_{20}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl;

$R_6$ is selected from null, $C_{1-20}$ alkyl, $C_{2-20}$ alkenyl, $C_1$-$C_{20}$ alkoxy, $C_{2-20}$ alkynyl, $C_{1-20}$ heteroalkyl, $C_{2-20}$ heteroalkenyl, $C_{2-20}$ heteroalkynyl, $C_6$-$C_{14}$ aryl, $C_1$-$C_{13}$ heteroaryl, $C_6$-$C_{14}$ aryloxy; wherein $R_6$ is optionally substituted with $C_1$-$C_{20}$ alkyl, $C_1$-$C_{20}$ alkoxy, $C_2$-$C_{20}$ alkenyl, $C_2$-$C_{20}$ alkynyl, $C_6$-$C_{14}$ aryl, $C_1$-$C_{13}$ heteroaryl, amino, carbonyl, ester, ether, halide, carboxyl, hydroxy, nitro, cyano, sulfo-oxo, sulfonyl, sulfone, sulfoxide, thiol, or phosphonyl; and $X_1$ and $X_2$ are protecting groups, each independently, selected from $C_6$-$C_{14}$ aryl, $C_1$-$C_{13}$ heteroaryl, $C_6$-$C_{14}$ aryloxy, benzyl, carbonyl, alkoxy, ether, cyclic ether; wherein each of $X_1$ and $X_2$ independent of each other is optionally substituted with $C_1$-$C_{20}$ alkyl, $C_1$-$C_{20}$ alkoxy, $C_2$-$C_{20}$ alkenyl, $C_2$-$C_{20}$ alkynyl, $C_6$-$C_{14}$ aryl, $C_1$-$C_{13}$ heteroaryl, amino, benzyl, carbonyl, ester, ether, halide, carboxyl, hydroxy, nitro, cyano, silyl, sulfo-oxo, sulfonyl, sulfone, sulfoxide, thiol, or phosphonyl.

The methods further comprise functionalizing the compound of formula (II) to obtain a compound of formula (I) as described above. Some additional exemplary methods are described in "Syntheses of polyalkylated imidazoles" by Sigvart Evjen et al., Synthetic Communications, 2017, 47, 1392-1399, which is incorporated herein by reference.

The examples below are intended to further illustrate certain aspects of the methods and compositions described herein and are not intended to limit the scope of the claims.

EXAMPLES

The following examples are set forth below to illustrate the methods and results according to the disclosed subject matter. These examples are not intended to be inclusive of all aspects of the subject matter disclosed herein but rather to illustrate representative methods and results. These examples are not intended to exclude equivalents and variations of the present invention, which are apparent to one skilled in the art.

Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions, that can be used to optimize the product purity and yield obtained from the described process. Only reasonable and routine experimentation will be required to optimize such process conditions.

Example 1

Synthesis of 1H-imidazol-2-yl-methanamine

In this example, an ethanolamine is reacted with 2 molecules of chloromethyl benzene, behaving as a protecting group to form N,N-dibenzylethanolamine, according to Scheme 1.

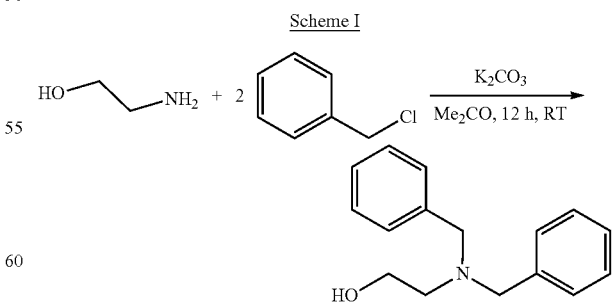

The N,N-dibenzylethanolamine is then oxidized to form an aldehyde using Swern oxidation reaction, and the formed aldehyde is reacted with glyoxal to form a 2-(N-Phenyl-N-benzyl-aminomethyl)-imidazol according to Scheme II:

Scheme II

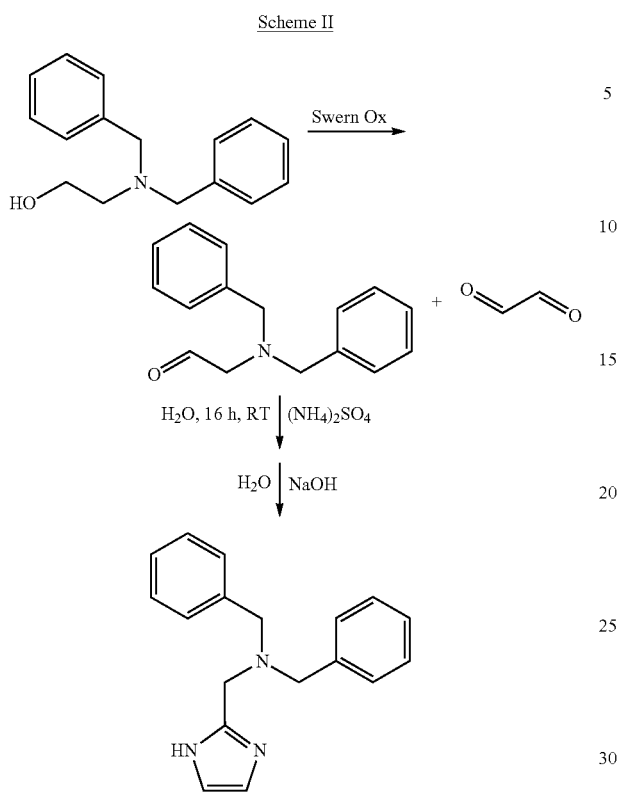

The protecting group can be removed by reducing the 2-(N-Phenyl-N-benzyl-aminomethyl)-imidazol in hydrogen over Pd/C catalyst, as seen in Scheme III.

Scheme III

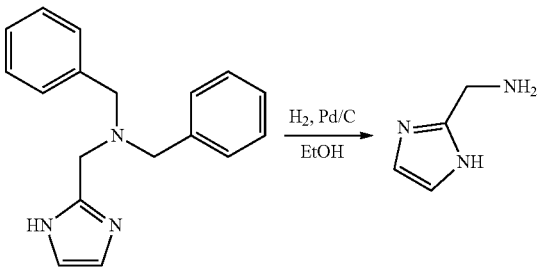

The claims are not intended to include, and should not be interpreted to include, means-plus- or step-plus-function limitations, unless such a limitation is explicitly recited in a given claim using the phrase(s) "means for" or "step for," respectively.

In view of the described processes and compositions, hereinbelow are described certain more particularly described aspects of the inventions. These particularly recited aspects should not, however, be interpreted to have any limiting effect on any different claims containing different or more general teachings described herein, or that the "particular" aspects are somehow limited in some way other than the inherent meanings of the language and formulas literally used therein.

Aspects

Aspect 1: A method of reducing one or more volatile compounds from a stream, comprising: contacting a stream with a solution comprising an imidazole having formula (I) and a solvent,

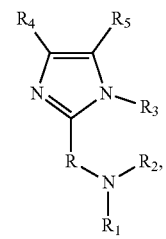

wherein

R is selected from null, $C_{1-20}$ alkyl, $C_{2-20}$ alkenyl, $C_1$-$C_{20}$ alkoxy, $C_{2-20}$ alkynyl, $C_{1-20}$ heteroalkyl, $C_{2-20}$ heteroalkenyl, $C_{2-20}$ heteroalkynyl, $C_6$-$C_{14}$ aryl, $C_1$-$C_{13}$ heteroaryl, $C_6$-$C_{14}$ aryloxy; wherein R is optionally substituted with $C_1$-$C_{20}$ alkyl, $C_1$-$C_{20}$ alkoxy, $C_2$-$C_{20}$ alkenyl, $C_2$-$C_{20}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl; and $R_1$ and $R_2$ are, independent of one another, hydrogen, $C_{1-20}$ alkyl, $C_{2-20}$ alkenyl, $C_1$-$C_{20}$ alkoxy, $C_{2-20}$ alkynyl, $C_{1-20}$ heteroalkyl, $C_{2-20}$ heteroalkenyl, $C_{2-20}$ heteroalkynyl, $C_6$-$C_{14}$ aryl, $C_1$-$C_{13}$ heteroaryl, $C_6$-$C_{14}$ aryloxy, carbonyl, ester, ether, halide, carboxyl, hydroxy, nitro, cyano, silyl, sulfo-oxo, sulfonyl, sulfone, sulfoxide, thiol, or phosphonyl; wherein each $R_1$ or $R_2$ independent of each other is optionally substituted with $C_1$-$C_{20}$ alkyl, $C_1$-$C_{20}$ alkoxy, $C_2$-$C_{20}$ alkenyl, $C_2$-$C_{20}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl; $R_3$ is selected from hydrogen, $C_1$-$C_{10}$ alkyl, $C_1$-$C_{10}$ alkoxy, $C_6$-$C_{14}$ aryl, $C_1$-$C_{13}$ heteroaryl, $C_6$-$C_{14}$ aryloxy, wherein $R_3$ is optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl; $R_4$ and $R_5$ are each independent of the other, selected from hydrogen, $C_{1-20}$ alkyl, $C_{2-20}$ alkenyl, $C_1$-$C_{20}$ alkoxy, $C_{2-20}$ alkynyl, $C_{1-20}$ heteroalkyl, $C_{2-20}$ heteroalkenyl, $C_{2-20}$ heteroalkynyl, $C_6$-$C_{14}$ aryl, $C_1$-$C_{13}$ heteroaryl, $C_6$-$C_{14}$ aryloxy, carbonyl, ester, ether, halide, carboxyl, hydroxy, nitro, cyano, silyl, sulfo-oxo, sulfonyl, sulfone, sulfoxide, thiol, or phosphonyl; wherein each $R_1$ or $R_2$ independent of each other is optionally substituted with $C_1$-$C_{20}$ alkyl, $C_1$-$C_{20}$ alkoxy, $C_2$-$C_{20}$ alkenyl, $C_2$-$C_{20}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl; or wherein $R^4$ and $R^5$ together form a 6 membered aromatic ring containing 6 carbon atoms.

Aspect 2: The method of Aspect 1, wherein the imidazole of formula (I) absorbs the one or more volatile compounds.

Aspect 3: The method of Aspect 1 or 2, wherein the imidazole of formula (I) forms at least one complex with the one or more volatile compounds.

Aspect 4: The method of Aspect 3, further comprising removing the at least one complex from the gas stream.

Aspect 5: The method of any one of Aspects 1-4, wherein the imidazole of formula (I) is non-ionic under neutral conditions.

Aspect 6: The method of any one of Aspects 1-5, wherein the stream comprises a flue gas.

Aspect 7: The method of any one of Aspects 1-6, wherein the one or more volatile compounds present in the stream comprise one or more of carbon dioxide, hydrogen sulfide, sulfur dioxide, nitrogen oxide, nitrogen dioxide, carbonyl sulfide, or carbon disulfide.

Aspect 8: The method of Aspect 7, wherein the volatile compound is carbon dioxide.

Aspect 9: The method of any one of Aspects 1-8, wherein R is selected from —$CH_2$—, —$CH(CH_3)$—, —$C(CH_3)_2$—, —$CH_2CH_2$—, —$CH_2CH(CH_3)$—, —$CH_2C(CH_3)_2$—, —$CH_2CH_2CH_2$, —$CH_2CH_2CH(CH_3)$—, or —$CH_2CH_2C(CH_3)_2$—.

Aspect 10: The method of any one of Aspects 1-9, wherein the imidazole of formula (I) is selected from

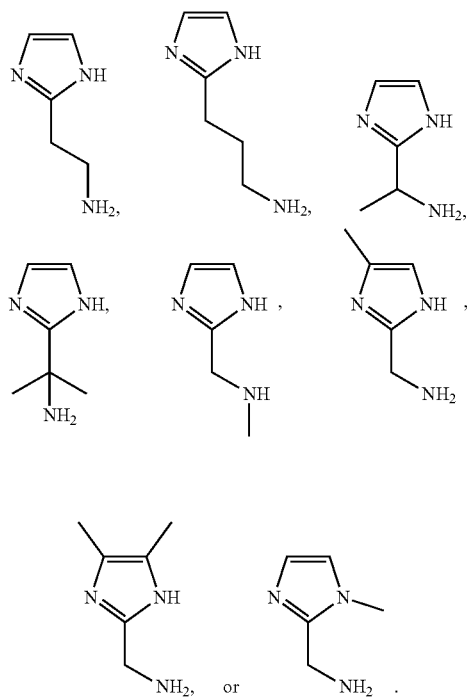

Aspect 11: The method of any one of Aspects 1-10, wherein the solvent comprises one or more of water, tetrahydrofuran, dichloromethane, acetonitrile, toluene, dimethyl sulfoxide, pyridine, dimethylformamide, dioxane, glycol solvents, methanol, ethanol, propanol, butanol, ethyl acetate, methyl ethyl ketone, or acetone.

Aspect 12: The method of Aspect 11, wherein the solvent comprises water.

Aspect 13: The method of any one of Aspects 1-8, wherein the imidazole of formula (I) is present in an amount from about 10 wt % to about 90 wt % in the solution.

Aspect 14: The method of any one of Aspects 8-13, wherein the imidazole of formula (I) absorbs carbon dioxide in a ratio of 1:3.

Aspect 15: A method for sweetening a natural gas feed stream, comprising: a) contacting the natural gas feed stream with a solution comprising an imidazole of formula (I) and a solvent,

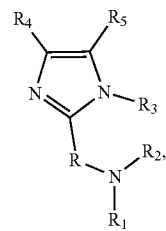

wherein

R is selected from null, $C_{1-20}$ alkyl, $C_{2-20}$ alkenyl, $C_1$-$C_{20}$ alkoxy, $C_{2-20}$ alkynyl, $C_{1-20}$ heteroalkyl, $C_{2-20}$ heteroalkenyl, $C_{2-20}$ heteroalkynyl, $C_6$-$C_{14}$ aryl, $C_1$-$C_{13}$ heteroaryl, $C_6$-$C_{14}$ aryloxy; wherein R is optionally substituted with $C_1$-$C_{20}$ alkyl, $C_1$-$C_{20}$ alkoxy, $C_2$-$C_{20}$ alkenyl, $C_2$-$C_{20}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl; and $R_1$ and $R_2$ are, independent of one another, hydrogen, $C_{1-20}$ alkyl, $C_{2-20}$ alkenyl, $C_1$-$C_{20}$ alkoxy, $C_{2-20}$ alkynyl, $C_{1-20}$ heteroalkyl, $C_{2-20}$ heteroalkenyl, $C_{2-20}$ heteroalkynyl, $C_6$-$C_{14}$ aryl, $C_1$-$C_{13}$ heteroaryl, $C_6$-$C_{14}$ aryloxy, carbonyl, ester, ether, halide, carboxyl, hydroxy, nitro, cyano, silyl, sulfo-oxo, sulfonyl, sulfone, sulfoxide, thiol, or phosphonyl; wherein each $R_1$ or $R_2$ independent of each other is optionally substituted with $C_{1-20}$ alkyl, $C_1$-$C_{20}$ alkoxy, $C_2$-$C_{20}$ alkenyl, $C_2$-$C_{20}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl; $R_3$ is selected from hydrogen, $C_1$-$C_{10}$ alkyl, $C_1$-$C_{10}$ alkoxy, $C_6$-$C_{14}$ aryl, $C_1$-$C_{13}$ heteroaryl, $C_6$-$C_{14}$ aryloxy, wherein $R_3$ is optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl; $R_4$ and $R_5$ are each independent of the other, selected from hydrogen, $C_{1-20}$ alkyl, $C_{2-20}$ alkenyl, $C_1$-$C_{20}$ alkoxy, $C_{2-20}$ alkynyl, $C_{1-20}$ heteroalkyl, $C_{2-20}$ heteroalkenyl, $C_{2-20}$ heteroalkynyl, $C_6$-$C_{14}$ aryl, $C_1$-$C_{13}$ heteroaryl, $C_6$-$C_{14}$ aryloxy, carbonyl, ester, ether, halide, carboxyl, hydroxy, nitro, cyano, silyl, sulfo-oxo, sulfonyl, sulfone, sulfoxide, thiol, or phosphonyl; wherein each $R_1$ or $R_2$ independent of each other is optionally substituted with $C_1$-$C_{20}$ alkyl, $C_1$-$C_{20}$ alkoxy, $C_2$-$C_{20}$ alkenyl, $C_2$-$C_{20}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl; or wherein $R_4$ and $R_5$ together form a 6 membered aromatic ring containing 6 carbon atoms; b) forming a purified gas feed stream and a gas-rich solution; and c) separating the purified gas feed stream and the gas-rich solution.

Aspect 16: The method of Aspect 15, wherein the imidazole of formula (I) is non-ionic under neutral conditions.

Aspect 17: The method of Aspect 15 or 16, wherein the natural gas feed stream comprises one or more volatile compounds comprising one or more of carbon dioxide, hydrogen sulfide, sulfur dioxide, nitrogen oxide, nitrogen dioxide, carbonyl sulfide, or carbon disulfide.

Aspect 18: The method of Aspect 17, wherein in step b) the one or more volatile compounds are transferred to the gas-rich solution.

Aspect 19: The method of any one of Aspects 17 or 18, wherein the one or more volatile compounds form at least one complex with the imidazole of formula (I).

Aspect 20: The method of any one of Aspects 15-19, wherein R is selected from —CH₂—, —CH(CH₃)—, —C(CH₃)₂—, —CH₂CH₂—, —CH₂CH(CH₃)—, —CH₂C(CH₃)₂—, —CH₂CH₂CH₂, —CH₂CH₂CH(CH₃)—, or —CH₂CH₂C(CH₃)₂—

Aspect 21: The method of any one of Aspects 15-20, wherein the imidazole of formula (I) is selected from

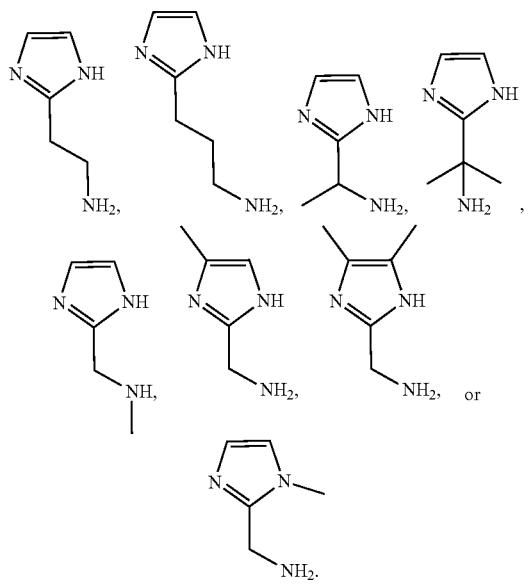

Aspect 22: The method of any one of Aspects 15-21, wherein the solvent comprises one or more of water, tetrahydrofuran, dichloromethane, acetonitrile, toluene, dimethyl sulfoxide, pyridine, dimethylformamide, dioxane, glycol solvents, methanol, ethanol, propanol, butanol, ethyl acetate, methyl ethyl ketone, or acetone.

Aspect 23: The method of Aspect 22, wherein the solvent comprises water

Aspect 24: The method of any one of claim Aspects 15-23, wherein the imidazole tethered to an amine is present in an amount from about 10 wt % to about 90 wt % in solution.

Aspect 25: A solution for the reduction of volatile compounds, comprising: a) an imidazole of formula (I),

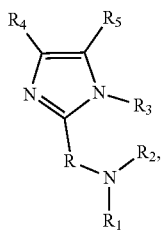

wherein
R is selected from null, $C_{1-20}$ alkyl, $C_{2-20}$ alkenyl, $C_{1-20}$ alkoxy, $C_{2-20}$ alkynyl, $C_{1-20}$ heteroalkyl, $C_{2-20}$ heteroalkenyl, $C_{2-20}$ heteroalkynyl, $C_6$-$C_{14}$ aryl, $C_1$-$C_{13}$ heteroaryl, $C_6$-$C_{14}$ aryloxy; wherein R is optionally substituted with $C_1$-$C_{20}$ alkyl, $C_1$-$C_{20}$ alkoxy, $C_2$-$C_{20}$ alkenyl, $C_2$-$C_{20}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl; and $R_1$ and $R_2$ are, independent of one another, hydrogen, $C_{1-20}$ alkyl, $C_{2-20}$ alkenyl, $C_1$-$C_{20}$ alkoxy, $C_{2-20}$ alkynyl, $C_{1-20}$ heteroalkyl, $C_{2-20}$ heteroalkenyl, $C_{2-20}$ heteroalkynyl, $C_6$-$C_{14}$ aryl, $C_6$-$C_{14}$ aryl, $C_1$-$C_{13}$ heteroaryl, $C_6$-$C_{14}$ aryloxy, carbonyl, ester, ether, halide, carboxyl, hydroxy, nitro, cyano, silyl, sulfo-oxo, sulfonyl, sulfone, sulfoxide, thiol, or phosphonyl; wherein each $R_1$ or $R_2$ independent of each other is optionally substituted with $C_1$-$C_{20}$ alkyl, $C_1$-$C_{20}$ alkoxy, $C_2$-$C_{20}$ alkenyl, $C_2$-$C_{20}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl; $R_3$ is selected from hydrogen, $C_1$-$C_{10}$ alkyl, $C_1$-$C_{10}$ alkoxy, $C_6$-$C_{14}$ aryl, $C_1$-$C_{13}$ heteroaryl, $C_6$-$C_{14}$ aryloxy, wherein $R_3$ is optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl; $R_4$ and $R_5$ are each independent of the other, selected from hydrogen, $C_{1-20}$ alkyl, $C_{2-20}$ alkenyl, $C_1$-$C_{20}$ alkoxy, $C_{2-20}$ alkynyl, $C_{1-20}$ heteroalkyl, $C_{2-20}$ heteroalkenyl, $C_{2-20}$ heteroalkynyl, $C_6$-$C_{14}$ aryl, $C_1$-$C_{13}$ heteroaryl, $C_6$-$C_{14}$ aryloxy, carbonyl, ester, ether, halide, carboxyl, hydroxy, nitro, cyano, silyl, sulfo-oxo, sulfonyl, sulfone, sulfoxide, thiol, or phosphonyl; wherein each $R_1$ or $R_2$ independent of each other is optionally substituted with $C_1$-$C_{20}$ alkyl, $C_1$-$C_{20}$ alkoxy, $C_2$-$C_{20}$ alkenyl, $C_2$-$C_{20}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl; or wherein $R_4$ and $R_5$ together form a 6 membered aromatic ring containing 6 carbon atoms; and b) solvent.

Aspect 26: The solution of Aspect 25, wherein the imidazole formula (I) is non-ionic under neutral conditions.

Aspect 27: The solution of Aspect 25 or 26, wherein the solution is configured to absorb one or more volatile compounds comprising carbon dioxide, hydrogen sulfide, sulfur dioxide, nitrogen oxide, nitrogen dioxide, carbonyl sulfide, carbon disulfide, or mixtures thereof.

Aspect 28: The solution of any one of Aspects 25-27, wherein the solvent comprises one or more of water, tetrahydrofuran, dichloromethane, acetonitrile, toluene, dimethyl sulfoxide, pyridine, dimethylformamide, dioxane, glycol solvents, methanol, ethanol, propanol, butanol, ethyl acetate, methyl ethyl ketone, or acetone.

Aspect 29: The solution of any one of Aspects 25-28, wherein R is selected from —CH₂—, —CH(CH₃)—, —C(CH₃)₂—, —CH₂CH₂—, —CH₂CH(CH₃)—, —CH₂C(CH₃)₂—, —CH₂CH₂CH₂, —CH₂CH₂CH(CH₃)—, or —CH₂CH₂C(CH₃)₂—.

Aspect 30: The solution of any one of Aspects 25-29, wherein the imidazole of formula (I) is selected from

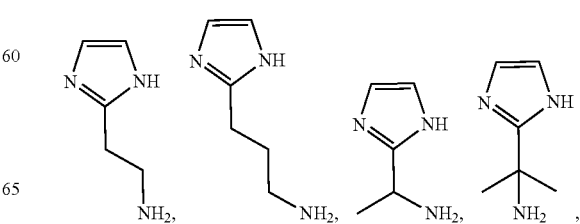

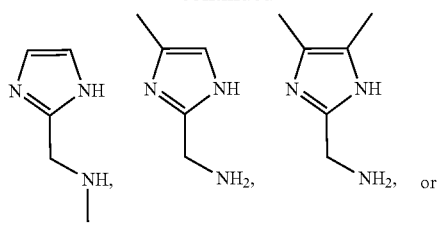

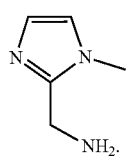

Aspect 31: The solution of any one of Aspects 25-30, wherein the imidazole of formula (I) is present in an amount from about 10 wt % to about 90 wt % in solution.

Aspect 32: A method of making an imidazole compound of formula (II) comprising: oxidizing a compound having a general formula of (III)

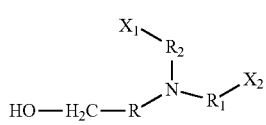

to form an aldehyde of general formula (IV):

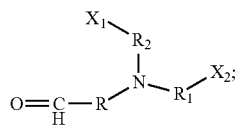

a) reacting the aldehyde of formula (IV) with a dialdehyde compound of formula (V)

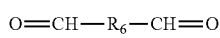

and an ammonium salt to form a compound of general formula (VI):

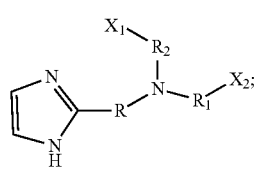

b) deprotecting the compound of formula (VI) to form the compound of formula (II):

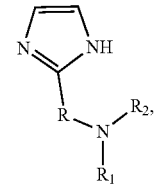

wherein

R is selected from null, $C_{1-20}$ alkyl, $C_{2-20}$ alkenyl, $C_1$-$C_{20}$ alkoxy, $C_{2-20}$ alkynyl, $C_{1-20}$ heteroalkyl, $C_{2-20}$ heteroalkenyl, $C_{2-20}$ heteroalkynyl, $C_6$-$C_{14}$ aryl, $C_1$-$C_{13}$ heteroaryl, $C_6$-$C_{14}$ aryloxy; wherein R is optionally substituted with $C_1$-$C_{20}$ alkyl, $C_1$-$C_{20}$ alkoxy, $C_2$-$C_{20}$ alkenyl, $C_2$-$C_{20}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl; and $R_1$ and $R_2$ are, independent of one another, hydrogen, $C_{1-20}$ alkyl, $C_{2-20}$ alkenyl, $C_1$-$C_{20}$ alkoxy, $C_{2-20}$ alkynyl, $C_{1-20}$ heteroalkyl, $C_{2-20}$ heteroalkenyl, $C_{2-20}$ heteroalkynyl, $C_6$-$C_{14}$ aryl, $C_1$-$C_{13}$ heteroaryl, $C_6$-$C_{14}$ aryloxy, carbonyl, ester, ether, halide, carboxyl, hydroxy, nitro, cyano, silyl, sulfo-oxo, sulfonyl, sulfone, sulfoxide, thiol, or phosphonyl; wherein each $R_1$ or $R_2$ independent of each other is optionally substituted with $C_1$-$C_{20}$ alkyl, $C_1$-$C_{20}$ alkoxy, $C_2$-$C_{20}$ alkenyl, $C_2$-$C_{20}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl;

What is claimed is:

1. A method of reducing one or more volatile compounds from a stream, comprising:
    contacting a stream with a solution consisting of an imidazole having formula (I) or a salt thereof, and a solvent,

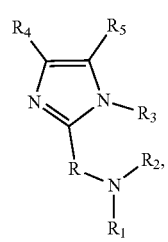

wherein

R is selected from null, $C_{1-20}$ alkyl, $C_{2-20}$ alkenyl, $C_1$-$C_{20}$ alkoxy, $C_{2-20}$ alkynyl, $C_{1-20}$ heteroalkyl, $C_{2-20}$ heteroalkenyl, $C_{2-20}$ heteroalkynyl, $C_6$-$C_{14}$ aryl, $C_1$-$C_{13}$ heteroaryl, $C_6$-$C_{14}$ aryloxy; wherein R is optionally substituted with $C_1$-$C_{20}$ alkyl, $C_1$-$C_{20}$ alkoxy, $C_2$-$C_{20}$ alkenyl, $C_2$-$C_{20}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl; and $R_1$ and $R_2$ are, independent of one another, hydrogen, $C_{1-20}$ alkyl, $C_{2-20}$ alkenyl, $C_1$-$C_{20}$ alkoxy, $C_{2-20}$ alkynyl, $C_{1-20}$ heteroalkyl, $C_{2-20}$ heteroalkenyl, $C_{2-20}$ heteroalkynyl, $C_6$-$C_{14}$ aryl, $C_1$-$C_{13}$ heteroaryl, $C_6$-$C_{14}$ aryloxy, carbonyl, ester, ether, halide, carboxyl, hydroxy, nitro, cyano, silyl, sulfo-oxo, sulfonyl, sulfone, sulfoxide, thiol, or phosphonyl; wherein each $R_1$ or $R_2$ independent of each other is optionally substituted with $C_1$-$C_{20}$ alkyl, $C_1$-$C_{20}$ alkoxy, $C_2$-$C_{20}$ alkenyl, $C_2$-$C_{20}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl;

$R_3$ is selected from hydrogen, $C_1$-$C_{10}$ alkyl, $C_1$-$C_{10}$ alkoxy, $C_6$-$C_{14}$ aryl, $C_1$-$C_{13}$ heteroaryl, $C_6$-$C_{14}$ aryloxy, wherein $R_3$ is optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl;

$R_4$ and $R_5$ are each independent of the other, selected from hydrogen, $C_{1-20}$ alkyl, $C_{2-20}$ alkenyl, $C_1$-$C_{20}$ alkoxy, $C_{2-20}$ alkynyl, $C_{1-20}$ heteroalkyl, $C_{2-20}$ heteroalkenyl, $C_{2-20}$ heteroalkynyl, $C_6$-$C_{14}$ aryl, $C_1$-$C_{13}$ heteroaryl, $C_6$-$C_{14}$ aryloxy, carbonyl, ester, ether, halide, carboxyl, hydroxy, nitro, cyano, silyl, sulfo-oxo, sulfonyl, sulfone, sulfoxide, thiol, or phosphonyl; wherein each $R_1$ or $R_2$ independent of each other is optionally substituted with $C_1$-$C_{20}$ alkyl, $C_1$-$C_{20}$ alkoxy, $C_2$-$C_{20}$ alkenyl, $C_2$-$C_{20}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl; or wherein $R_4$ and $R_5$ together form a 6 membered aromatic ring containing 6 carbon atoms, wherein the solvent consists essentially of water.

2. The method of claim 1, wherein the imidazole of formula (I) forms at least one complex with the one or more volatile compounds, and wherein the method further comprises removing the at least one complex from the stream.

3. The method of claim 1, wherein the imidazole of formula (I) is non-ionic under neutral conditions.

4. The method of claim 1, wherein the one or more volatile compounds present in the stream comprise one or more of carbon dioxide, hydrogen sulfide, sulfur dioxide, nitrogen oxide, nitrogen dioxide, carbonyl sulfide, or carbon disulfide.

5. The method of claim 1, wherein R is selected from —$CH_2$—, —$CH(CH_3)$—, —$C(CH_3)_2$—, —$CH_2CH_2$—, —$CH_2CH(CH_3)$—, —$CH_2C(CH_3)_2$—, —$CH_2CH_2CH_2$—, —$CH_2CH_2CH(CH_3)$—, or —$CH_2CH_2C(CH_3)_2$—.

6. The method of claim 1, wherein the imidazole of formula (I) is selected from

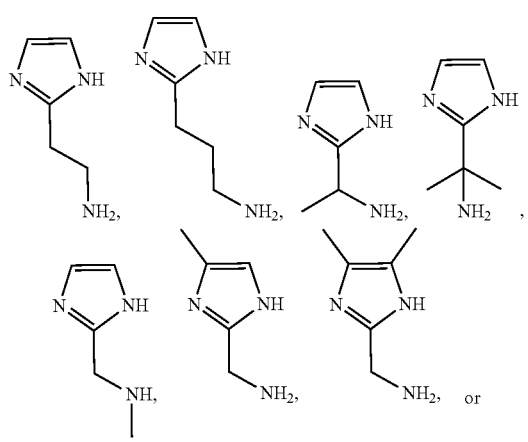

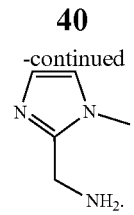

7. The method of claim 1, wherein the imidazole of formula (I) is present in the solution in an amount from about 30 wt % to about 70%.

8. The method of claim 4 wherein when the volatile compound is carbon dioxide, the imidazole of formula (I) absorbs carbon dioxide in a ratio of 1:3.

9. A method for sweetening a natural gas feed stream, comprising:
a) contacting the natural gas feed stream with a solution consisting of an imidazole of formula (I) or a salt thereof, and a solvent,

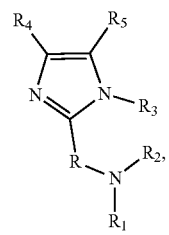

wherein

R is selected from null, $C_{1-20}$ alkyl, $C_{2-20}$ alkenyl, $C_1$-$C_{20}$ alkoxy, $C_{2-20}$ alkynyl, $C_{1-20}$ heteroalkyl, $C_{2-20}$ heteroalkenyl, $C_{2-20}$ heteroalkynyl, $C_6$-$C_{14}$ aryl, $C_1$-$C_{13}$ heteroaryl, $C_6$-$C_{14}$ aryloxy; wherein R is optionally substituted with $C_1$-$C_{20}$ alkyl, $C_1$-$C_{20}$ alkoxy, $C_2$-$C_{20}$ alkenyl, $C_2$-$C_{20}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl; and $R_1$ and $R_2$ are, independent of one another, hydrogen, $C_{1-20}$ alkyl, $C_{2-20}$ alkenyl, $C_1$-$C_{20}$ alkoxy, $C_{2-20}$ alkynyl, $C_{1-20}$ heteroalkyl, $C_{2-20}$ heteroalkenyl, $C_{2-20}$ heteroalkynyl, $C_6$-$C_{14}$ aryl, $C_1$-$C_{13}$ heteroaryl, $C_6$-$C_{14}$ aryloxy, carbonyl, ester, ether, halide, carboxyl, hydroxy, nitro, cyano, silyl, sulfo-oxo, sulfonyl, sulfone, sulfoxide, thiol, or phosphonyl; wherein each $R_1$ or $R_2$ independent of each other is optionally substituted with $C_1$-$C_{20}$ alkyl, $C_1$-$C_{20}$ alkoxy, $C_2$-$C_{20}$ alkenyl, $C_2$-$C_{20}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl;

$R_3$ is selected from hydrogen, $C_1$-$C_{10}$ alkyl, $C_1$-$C_{10}$ alkoxy, $C_6$-$C_{14}$ aryl, $C_1$-$C_{13}$ heteroaryl, $C_6$-$C_{14}$ aryloxy, wherein $R_3$ is optionally substituted with $C_1$-$C_{10}$ alkyl, $C_1$-$C_{10}$ alkoxy, $C_2$-$C_{10}$ alkenyl, $C_2$-$C_{10}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl;

$R_4$ and $R_5$ are each independent of the other, selected from hydrogen, $C_{1-20}$ alkyl, $C_{2-20}$ alkenyl, $C_1$-$C_{20}$ alkoxy, $C_{2-20}$ alkynyl, $C_{1-20}$ heteroalkyl, $C_{2-20}$ heteroalkenyl, $C_{2-20}$ heteroalkynyl, $C_6$-$C_{14}$ aryl, $C_1$-$C_{13}$ heteroaryl, $C_6$-$C_{14}$ aryloxy, carbonyl, ester, ether, halide, carboxyl, hydroxy, nitro, cyano, silyl, sulfo-oxo, sulfonyl, sulfone, sulfoxide, thiol, or phosphonyl; wherein each $R_1$ or $R_2$ independent of each other is optionally substituted with $C_1$-$C_{20}$ alkyl, $C_1$-$C_{20}$ alkoxy, $C_2$-$C_{20}$ alkenyl, $C_2$-$C_{20}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl; or wherein $R_4$ and $R_5$ together form a 6 membered aromatic ring containing 6 carbon atoms, wherein the solvent consists essentially of water;

b) forming a purified gas feed stream and a gas-rich solution; and c) separating the purified gas feed stream and the gas-rich solution.

10. The method of claim 9, wherein the imidazole of formula (I) is non-ionic under neutral conditions.

11. The method of claim 9, wherein the natural gas feed stream comprises one or more volatile compounds comprising one or more of carbon dioxide, hydrogen sulfide, sulfur dioxide, nitrogen oxide, nitrogen dioxide, carbonyl sulfide, or carbon disulfide.

12. The method of claim 11, wherein in step b) the one or more volatile compounds are transferred to the gas-rich solution.

13. The method of claim 11, wherein the one or more volatile compounds form at least one complex with the imidazole of formula (I).

14. The method of claim 9, wherein R is selected from —CH₂—, —CH(CH₃)—, —C(CH₃)₂—, —CH₂CH₂—, —CH₂CH(CH₃)—, —CH₂C(CH₃)₂—, —CH₂CH₂CH₂, —CH₂CH₂CH(CH₃)—, or —CH₂CH₂C(CH₃)₂—.

15. The method of claim 9, wherein the imidazole of formula (I) is selected from

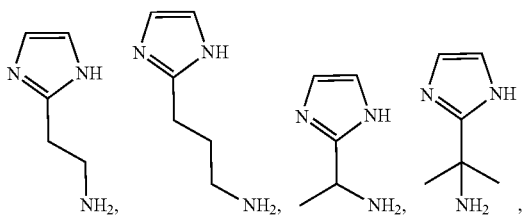

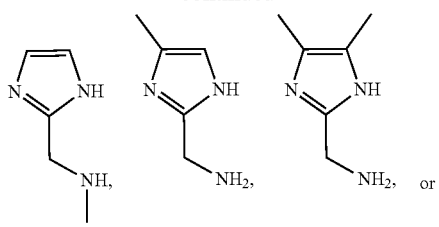

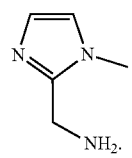

16. The method of claim 9, wherein the imidazole tethered to an amine is present in the solution in an amount from about 30 wt % to about 70 wt %.

17. The method of claim 1 wherein the imidazole of formula (I) is present in the solution in an amount from about 50 wt % to about 90 wt %.

18. The method of claim 9 wherein the imidazole of formula (I) is present in the solution in an amount from about 50 wt % to about 90 wt %.

19. The method of claim 1, wherein the imidazole having formula (I) is a basic salt.

20. The method of claim 1, wherein the imidazole having formula (I) is an alkali salt.

21. The method of claim 1, wherein the imidazole having formula (I) is a sodium salt.

22. The method of claim 9, wherein the imidazole having formula (I) is a basic salt.

23. The method of claim 9, wherein the imidazole having formula (I) is an alkali salt.

24. The method of claim 9, wherein the imidazole having formula (I) is a sodium salt.

* * * * *